US007749528B2

(12) United States Patent
De Carvalho et al.

(10) Patent No.: US 7,749,528 B2
(45) Date of Patent: *Jul. 6, 2010

(54) IMPLANTABLE AND SEALABLE MEDICAL DEVICE FOR UNIDIRECTIONAL DELIVERY OF THERAPEUTIC AGENTS TO TISSUES

(76) Inventors: Ricardo Azevedo Pontes De Carvalho, 600 N. Wolfe St., Maumenee Building, Suite 517, Baltimore, MD (US) 21287-9237; Alan Linn Murphree, 80 N. Euclid Ave., Pasadena, CA (US) 91101; Edward E. Schmitt, 600 N. Wolfe St., Maumenee Building, Suite 517, Baltimore, MD (US) 21287-9237

(*) Notice: Subject to any disclaimer, the term of this patent is extended or adjusted under 35 U.S.C. 154(b) by 1480 days.

This patent is subject to a terminal disclaimer.

(21) Appl. No.: 10/801,508

(22) Filed: Mar. 15, 2004

(65) Prior Publication Data
US 2005/0113806 A1   May 26, 2005

Related U.S. Application Data

(63) Continuation-in-part of application No. 10/231,767, filed on Aug. 28, 2002, now Pat. No. 7,195,774.

(60) Provisional application No. 60/315,952, filed on Aug. 29, 2001.

(51) Int. Cl.
*A61K 9/22* (2006.01)
*A61F 2/00* (2006.01)
(52) U.S. Cl. .................................. 424/423; 424/427
(58) Field of Classification Search ............ 424/422, 424/423, 424, 427, 433, 434, 448; 604/288.01, 604/288.02, 288.03, 288.04
See application file for complete search history.

(56) References Cited

U.S. PATENT DOCUMENTS

| 3,313,289 | A | * | 4/1967 | Kapral | 604/288.04 |
| 3,367,332 | A | * | 2/1968 | Groves | 604/290 |
| 3,797,485 | A | * | 3/1974 | Urquhart | 604/288.04 |
| 4,309,776 | A |   | 1/1982 | Berguer |   |
| 4,378,016 | A |   | 3/1983 | Loeb |   |
| 4,479,796 | A |   | 10/1984 | Kallok |   |

(Continued)

FOREIGN PATENT DOCUMENTS

CA    2399057    8/2001

(Continued)

OTHER PUBLICATIONS

WO 2004/073551 A3, International Search Report, Sep. 2, 2004.

(Continued)

*Primary Examiner*—Shanon A Foley
*Assistant Examiner*—Sarah Al-Awadi
(74) *Attorney, Agent, or Firm*—Daniel B. Schein, Esq.

(57) ABSTRACT

A device for selective delivery of therapeutic agents to internal body tissues is disclosed. Upon tight sealing of the device to targeted tissues the diffusion of therapeutic agents to the targeted tissue can be controlled, while minimizing exposure of adjacent organs to the agents being delivered. Mechanisms for replenishment of the device and methods for application of the device in remote sites of the body are disclosed.

34 Claims, 21 Drawing Sheets

U.S. PATENT DOCUMENTS

| | | | | |
|---|---|---|---|---|
| 4,605,399 | A | * | 8/1986 | Weston et al. ............... 604/305 |
| 5,182,111 | A | | 1/1993 | Aebischer et al. |
| 5,330,767 | A | * | 7/1994 | Yamamoto et al. .......... 424/497 |
| 5,399,352 | A | * | 3/1995 | Hanson ....................... 424/423 |
| 5,411,550 | A | | 5/1995 | Herweck et al. |
| 5,527,307 | A | * | 6/1996 | Srisathapat et al. ....... 604/892.1 |
| 5,725,493 | A | | 3/1998 | Avery et al. |
| 5,755,780 | A | * | 5/1998 | Finch et al. ................ 623/1.24 |
| 5,830,173 | A | | 11/1998 | Avery et al. |
| 5,836,935 | A | | 11/1998 | Ashton et al. |
| 5,902,598 | A | | 5/1999 | Chen et al. |
| 6,001,386 | A | | 12/1999 | Ashton et al. |
| 6,152,898 | A | * | 11/2000 | Olsen ....................... 604/93.01 |
| 6,217,895 | B1 | | 4/2001 | Guo et al. |
| 6,251,090 | B1 | | 6/2001 | Avery et al. |
| 6,287,293 | B1 | * | 9/2001 | Jones et al. ............... 604/891.1 |
| 6,413,540 | B1 | | 7/2002 | Yaacobi |
| 6,416,777 | B1 | | 7/2002 | Yaacobi |
| 2003/0064088 | A1 | | 4/2003 | Carvalho et al. |
| 2003/0069560 | A1 | | 4/2003 | Adamis et al. |
| 2004/0230183 | A1 | | 11/2004 | Breegi et al. |

FOREIGN PATENT DOCUMENTS

| | | |
|---|---|---|
| WO | WO 01/28472 | 4/2001 |
| WO | WO 03/020172 A1 | 3/2003 |
| WO | WO 2004/073551 A2 | 9/2004 |

OTHER PUBLICATIONS

WO 2004/073551 A2, Written Opinion of Patentability for PCT/US2004/004625, Aug. 19, 2005.

Valtonen, Simo., et al., Interstitial Chemotherapy with Carmustine-loaded Polymers for Highgrade Gliomas: A Randomized Double-blind Study Clinical Study, Neurosurgery, vol. 41, No. 1,pp. 44-52 (1997).

D'Hermies, Francois., et al., "Encapsulation of Scleral Buckling Materials", Ophthamology, vol. 105, No. 6. pp. 1079-1087 (1998).

Sayanl, A. et al., "Systemic Delivery of Peptides and Proteins Across Absorpive Mucosae", Therapeutic Reviews™ In Therapeutic Drug Carrier Systems. 13(1&2): 84-185 (1996).

Robinson, Michael R. et al., "A rabbit model for assessing the ocular barriers to the transscleral delivery of triamcinolone acetonide", Elsevier Ltd., pp. 1-9 (2005).

Pontes de Carvalho, Ricardo A. et al., "Delivery from Episcleral Exoplants", Invest. Ophthalmol. Vis. Sci..2006; 47: 4532-4539 (2006).

U.S. Appl. No. 60/334,177, filed Nov. 29, 2001, Borenstein et al.
U.S. Appl. No. 60/332,200, filed Nov. 21, 2001, Borenstein et al.
U.S. Appl. No. 60/332,199, filed Nov. 21, 2001, Borenstein et al.
U.S. Appl. No. 60/291,445, filed May 16, 2001, Borenstein et al.
U.S. Appl. No. 60/291,340, filed May 16, 2001, Borenstein et al.
U.S. Appl. No. 60/288,373, filed May 3, 2001, Borenstein et al.

Torres-Lugo, Madeline., et al., "Transmucosal delivery systems for calcitonin: a review", Biomaterials, vol. 21, pp. 1191-1196 (2000).

Benes, L., et al., "Transmucosal, Oral Controlled-Release, and Transdermal Drug Administration in Human Subjects: A Crossover Study with Melatonin", Journal of Pharmaceutical Sciences, vol. 86, No. 10, pp. 1115-1119 (1997).

Gebhardt, Bryan M., et al., "Collagen as a Delivery System for Hydrophobic Drugs: Studies with Cyclosporine", Journal of Ocular Pharmacology and Therapeutics, vol. 11, No. 3, pp. 319-327 (1995).

Kanpolat, Ayfer., et al., "Penetration of Cyclosporin A into the Rabbit Cornea and Aqueous Humor after Topical Drop and Collagen Shield Administration", The CLAO Journal, vol. 20, No. 2, pp. 119-122 (1994).

Lehr, C-M., "From sticky stuff to sweet receptors—Achievements, limits and novel approaches to bioadhesion", European Journal of Drug Metabolism and Pharmacokinetics, vol. 21, No. 2, pp. 139-148 (1996).

Rudnick, David E., et al., "The effect of Intraocular Pressure on Human and Rabbit Scleral Permeability", IOVS, vol. 40, No. 12, pp. 3054-3058 (1999).

Olsen, Timothy W., et al., "Human Sclera: Thickness and Surface Area", American Journal of Ophthalmology, vol. 125, No. 2, pp. 237-241 (1998).

Olsen, Timothy W., et al., "Human Scleral Permeability", Investigative Ophthalmology & Visual Science, vol. 36, No. 9, pp. 1893-1903 (1995).

Brem, Henry., et al., "Placebo-controlled trial of safety and efficacy of intraoperative controlled delivery by biodegradable polymers of chemotherapy for recurrent gliomas", The Lancet, vol. 345, pp. 1008-1012 (1995).

Valtonen, Simo., et al., Interstitial Chemotherapy with Carmustine-loaded Polymers for High-grade Gliomas: A Randomized Double-blind Study Clinical Study, Neurosurgery, vol. 41, No. 1, pp. 44-49 (1997).

Subach, Brian R., et al., "Morbidity and Survival after 1,3-bis(-chloroethyl)-1- Nitrosourea Wafer Implantation for Recurrent Glioblastoma: A Retrospective Case-matched cohort series", Neurosurgery, vol. 45, No. 1, pp. 17-23 (1999).

Moriya, T., et al., "Controlling Malignant Pericardial Effusion by Intrapericardial carboplatin Administration in Patients with Primary Non-Small-Cell Lung Cancer", British Journal of Cancer, vol. 83, No. 7, pp. 858-862 (2000).

Lerner-Tung, Mary B., et al., "Pharmacokinetics of intrapericardial administration of 5-fluorouracil", Cancer Chemother Pharmacol, vol. 40, pp. 318-320 (1997).

Darsinos, J. Th., et al., "Distribution of lidocaine and digoxin in heart tissues and aorta following intrapericardial administration", International Journal of Clinical Pharmacology, Therapy and Toxicology, vol. 31, No. 12, pp. 611-615 (1993).

Darsinos, J. T., et al., "Distribution of amiodarone in heart tissues following intrapericardial administration", International Journal of Clinical Pharmacology and Therapeutics, vol. 37, No. 6, pp. 301-306 (1999).

Uchida,Y., et al., "Angiogenic therapy of acute myocardial infarction by intrapericardial injection of basic fibroblast growth factor and heparin sulfate: An experimental study", American Heart Journal, vol. 36, No. 6, pp. 1182-1188 (1995).

Laham, Roger J., "Intrapericardial Administration of Basic Fibroblast Growth Factor: Myocardial and Tissue Distribution and Comparison With Intracoronary and Intravenous Administration", Catheterization and Cardiovascular Interventions, vol. 58, pp. 375-381 (2003).

D'Hermies, Francois., et al., "Scleral and episcleral histological changes related to encircling explants in 20 eyes", ACTA Ophthalmologica Scandinavica, vol. 77, pp. 279-285 (1999).

D'Hermies, Francois., et al., "Encapsulation of Scleral Buckling Materials", Ophthamology, vol. 105, No. 6. (1998).

Ricci, Benedetto., et al., "Octyl 2-cyanoacrylate tissue adhesive in experimental scleral buckling", Acta Ophthalmol. Scand., vol. 78, pp. 506-508 (2001).

Korobelnik, J. F., "Expanded Polytetrafluoroethylene Episcleral Implants Used as Encircling Scleral Buckling", Opthalmic Res, vol. 32, pp. 110-117 (2000).

Mulvihill, Alan., et al. "Ocular Motility Changes After Subtenon Carboplatin Chemotherapy for Retinoblastoma", Arch Ophthalmo. vol. 121, pp. 1120-1124 (2003).

D'Hermies, F., "Alterations Anatomopathologiques Liees Au Traitement Par Cerclage Des Golbes Oculaires Atteints De Decollement De Retine", Societe D'ecition de l'Association de 'Enseignement Medical des Hopitaux de Paris. pp. 215-222 (1999).

Korobelnik, J. F. et al., "e-PTFE as Scleral Buckling Episcleral Implants: An Experimental and Histopathologic Study", John Wiley & Sons, Inc. J Biomed Mater Res vol. 48, pp. 807-813 (1999).

D'Hermies, F. et al., "Experimental Encircling Scleral Buckle With Silicone and Hydrogel", The Journal of Retinal and Vitreous Diseases. vol. 19 No. 2, pp. 148-157, 1999.

D'Hermies, F. et al., "Miragel Versus Silastic Used As Episcleral Implants in Rabbits", Retina vol. 15 No. 1 pp. 62-67 (1995).

Spitznas, M. et al., "Retinal Surgery Using Cyanoacrylate as a Routine Procedure", Arch. Klin. exp. Ophtal. vol. 187, pp. 89-101 (1973).

Calabria, G. et al., "Sutureless Scleral Buckling", *Arch Ophthal.* vol. 83, pp. 613-618 (1970).

Calabria, G. et al., "Further Experience With Sutureless Scleral Buckling Materials", *Arch Ophthal.* vol. 86, pp. 82-87 (1971).

Olsen, T.W. et al., "An Evaluation of an Episcleral Anecortave Acetate Transscleral Drug Delivery System in Rhesus Monkey", *Invest Ophthalmol Vis Sci.* vol. 44, p. 4213 (2003).

Yaacobi, Y. et al., "In-Vivo Studies with Trans-Scleral Anecortave Acetate Delivery Device Designed to Treat Choroidal Neovascularization in AMD", *Invest Ophthalmol Vis Sci.* vol. 44, p. 4210 (2003).

Olsen, T. et al., "Human Sclera: Thickness and Surface Area", *American Journal of Ophthalmology.* vol. 125. No. 2, pp. 237-241 (1998).

Harbour, J. et al., "Transducible Peptide Therapy for Uveal Melanoma and Retinoblastoma", *Arch Ophthalmol.* vol. 120, pp. 1341-1346 (2002).

Sayani, A. et al., "Systemic Delivery of Peptides and Proteins Across Absorptive Mucosae", *Therapeutic Reviews™ in Therapeutic Drug Carrier Systems.* 13(1&2): 84-185 (1996).

* cited by examiner

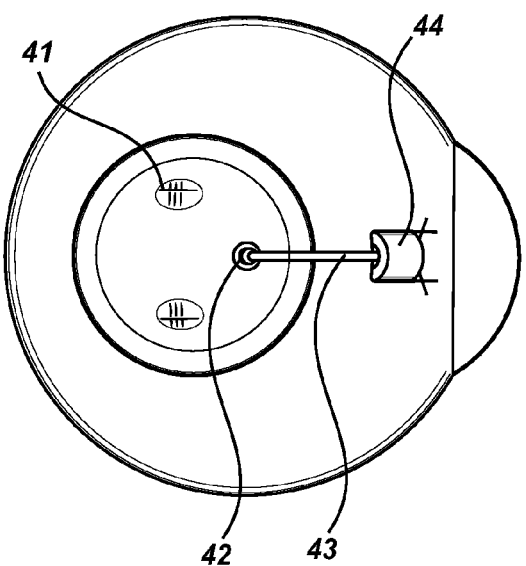
Fig. 16
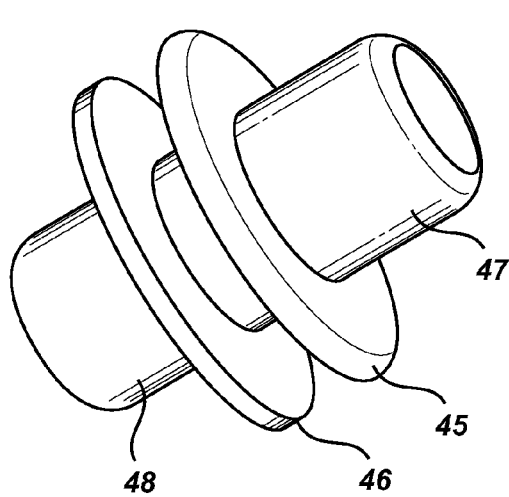 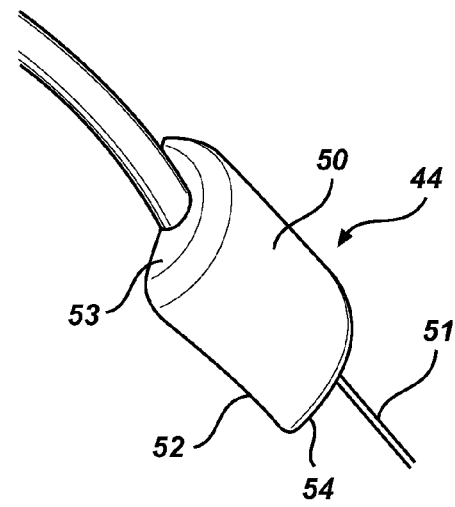
Fig. 17     Fig. 18

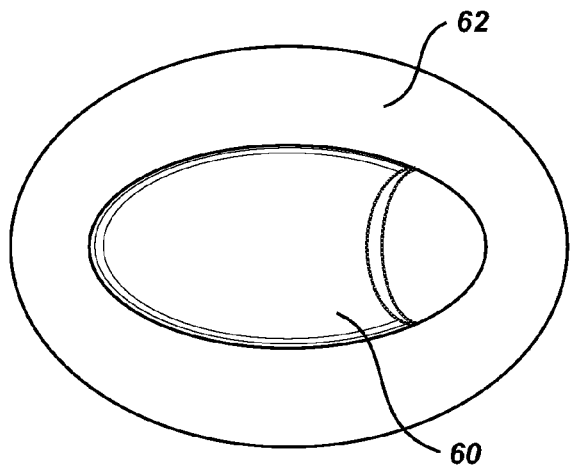
Fig. 21
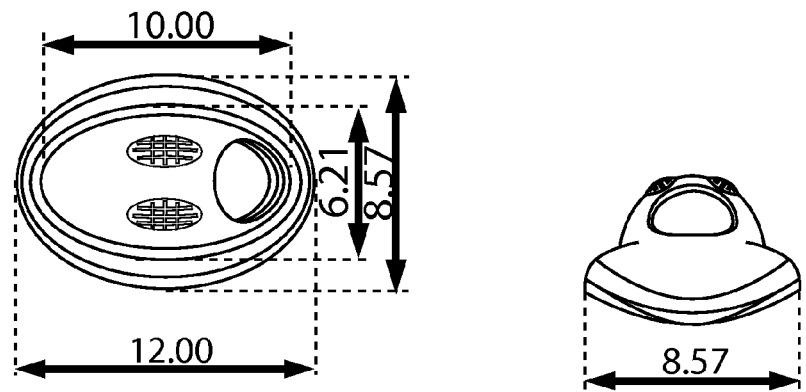
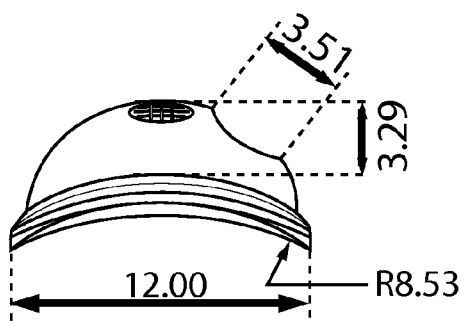
Fig. 22

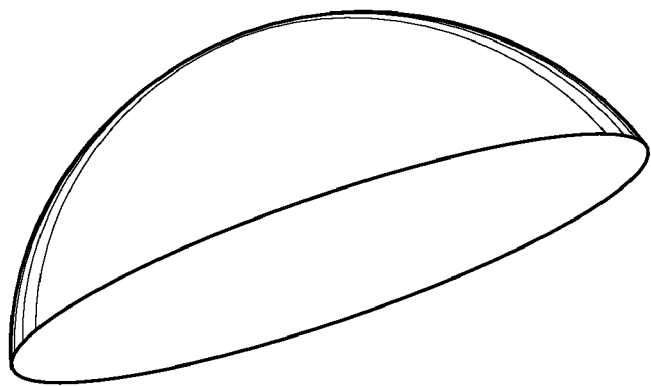
Fig. 40
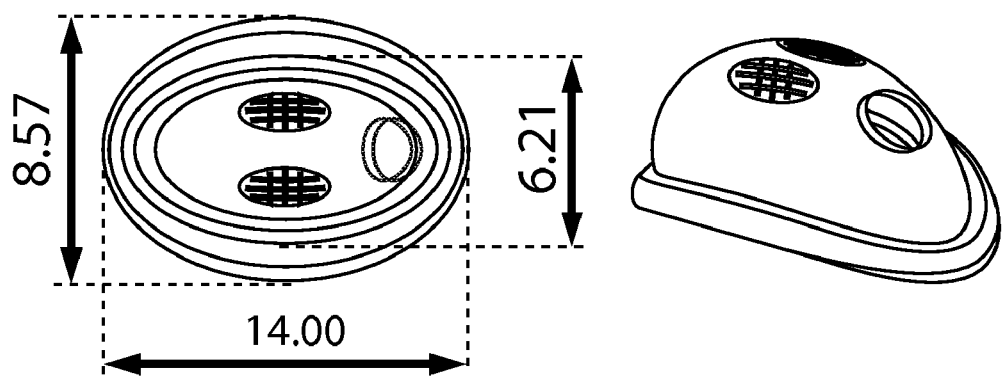
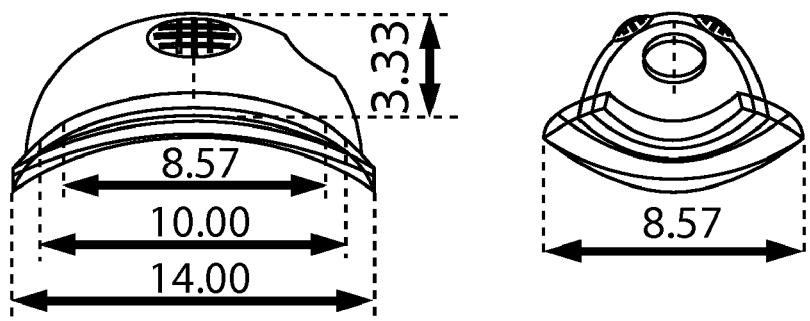
Fig. 41

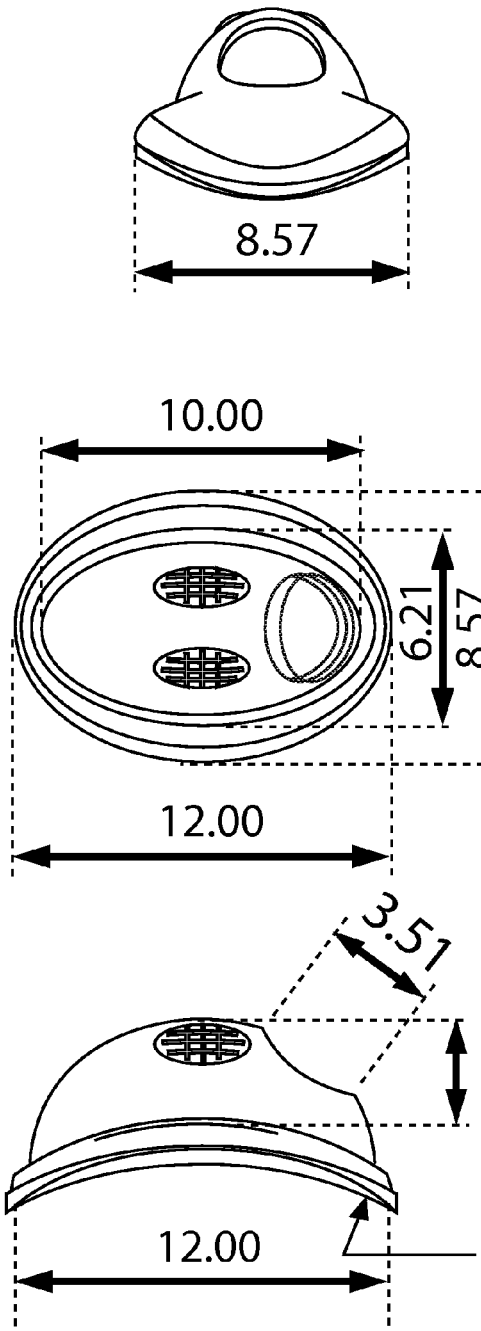
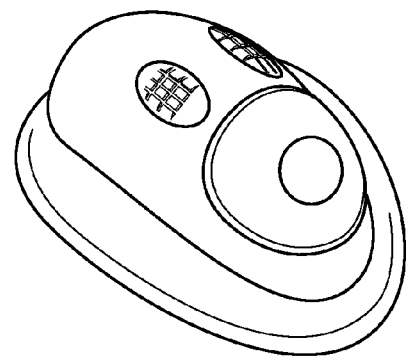
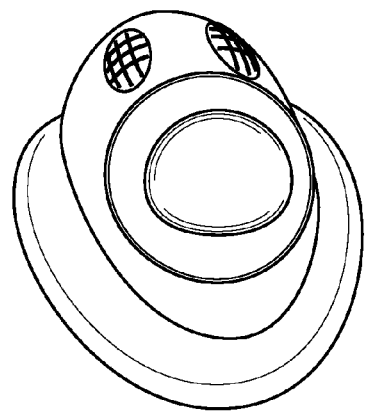
Fig. 43
Fig. 44
Fig. 45

IMPLANTABLE AND SEALABLE MEDICAL DEVICE FOR UNIDIRECTIONAL DELIVERY OF THERAPEUTIC AGENTS TO TISSUES

PRIORITY

This application is a continuation-in-part of U.S. patent application Ser. No. 10/231,767, filed Aug. 28, 2002, now U.S. Pat. No. 7,195,774 which claims priority of U.S. provisional patent application Ser. No. 60/315,952, filed Aug. 29, 2001, both of which are specifically incorporated by reference as if reproduced in full below.

FIELD OF THE INVENTION

The present invention relates to the field of drug delivery to organs and tissues of mammals. It also relates to devices aimed to selectively deliver therapeutic and diagnostic agents to targeted tissues and organs in mammalian organisms. The invention comprises design and methods to achieve and enhance therapeutic effects of drugs while minimizing deleterious effects to non-targeted body tissues.

BACKGROUND

The above-referenced application, U.S. PTO Ser. No. 10/231,767, filed on Aug. 28, 2003, discloses a device comprising a housing, wherein the housing comprises a reservoir member with a drug release port for release of at least a first therapeutic agent into a target tissue, said reservoir member having at least a first wall that is substantially impermeable to a first therapeutic agent to be placed therein, a sealing base for sealing said release port to a target tissue, wherein when said release port is sealed to a target tissue, a first therapeutic agent in said reservoir is substantially prohibited from release by said device other than through said release port into the target tissue, and an attachment mechanism to facilitate sealing of said release port to a target tissue, said attachment mechanism comprising at least one member of the group consisting of a sufficient amount of an adhesive for adhering said sealing base to a target tissue, a suture holder for engaging at least one suture operatively attached to the surrounding tissue, and an encircling band for engaging a fitting operatively attached to the surrounding target tissue.

Despite advances in screening and filtering of compounds during the drug development process, it is estimated that 99% of evaluated agents fail to reach clinical testing. Approximately 40% of the failures are due to poor pharmacokinetics and 11% to pre-clinical toxicity.[1,2] The search for new drugs is time-consuming and very expensive. Many drugs with proven therapeutic benefit for site-specific disease cannot be used clinically because of unacceptable systemic toxicity.

The value of local administration of therapeutic agents to organ-confined disease is demonstrated by the continuing efforts to improve local delivery to the eye. The ocular volume constitutes less than 1% of the body volume. When therapeutic agents are administered systemically for intraocular disease, most of the effect of the drugs is on normal non-ocular tissue.

The treatment of most diseases today requires a careful balance between the therapeutic efficacy of any specific agent and the unwanted side effects to be expected from its use. The intervals between cycles of chemotherapeutic agents for malignant disease are necessary to allow the body to recover from unwanted systemic toxicity. This cycling of treatment may not be the most efficacious way to deliver therapy to the disease but it cannot be avoided. The development of biotargeted agents promises some relief from the side effects of today's drugs on normal tissue. However, the costs associated with new agent development are enormous and their long-term side effects are not well understood.

Intraocular implants with sustained release of therapeutic agents were a great advance in the therapy of posterior segment (choroidal and retinal) ocular diseases. In most of these implants, the drug release rate is regulated mainly by the drug interaction with the polymer or coating membrane. The intravitreal route of drug delivery has limitations, however. If, as in the case of intraocular retinoblastoma, dissemination of tumor cells to the rest of the body is detrimental, then opening the eye for therapeutic reasons presents the risk of systemic dissemination of tumor cells. This limitation certainly applies to other tumors and other tissues. Moreover, intraocular procedures, regardless their purpose, require specialized expertise, and present inherent risks, such as endophthalmitis and retinal detachment.

U.S. Pat. Nos. 6,217,895; 6,001,386; 5,902,598; and 5,836,935, to Ashton et al. describe a surgically implantable device for local delivery of low solubility therapeutic agents in an internal portion of the body. The device comprises an inner core containing the drug isolated from the surrounding environment by a permeable coating polymer, which controls the release rate of the drug. The device delivers the drug in a multidirectional way from the implantation site, exposing the surrounding tissues to the delivered agent. It can be anchored to a tissue but no methods to seal it to a targeted tissue are disclosed.

Several studies were conducted to study potential advantages of the subconjunctival (periocular) injections of drugs over the topical (eyedrops) and systemic (intravenous) routes. Subconjunctival injections explore the diffusion properties of the sclera to drugs. Different drugs have been tested aiming for a improved pharmacokinetics in different layers of the eye. The results showed that a large variety of agents up to 40 kDa in size can diffuse across the sclera, in part because of the sclera's lack of binding sites. Similar evidence is available for several other organs and tissues. The injection of solutions containing drugs around or inside a tissue is a useful method to deliver drugs if their therapeutic effect in that tissue is transient, but repeated injections bring discomfort, pain and a higher risk of complications.

Moreover, subconjunctival injections lack specificity because the injected drugs diffuse to all the surrounding tissues, e.g. sclera, optic nerve, extraocular muscles and orbital fat and will interact in both a therapeutic and toxic way with all of them.

The subconjunctival delivery route does not address the fact that drugs have an acceptable rate of complications based on the benefits they provide to pathologic organs and tissues nor does it address the fact that the toxicity tolerated by normal tissues and organs is lower. The present invention described below can provide target-specificity based on topographic selectiveness even for nonspecific agents at the molecular level. As an example, it was shown that periocular injections of carboplatin can lead to ocular motility problems, including restriction of the eye movements, after a certain period following the injection. These complications are related to fibrosis of the periocular tissues caused by the inflammatory-inductor effect of carboplatin on normal surrounding tissue.(1)

U.S. Pat. Nos. 6,416,777 and 6,413,540, to Yaacobi et al., disclose devices that once positioned underneath the Tenon's capsule, in contact to the sclera, deliver agents to the eye. The device has a geometry that facilitates its insertion and placement in the sub-Tenon's space, and reference is made to a method to place and hold it under the inferior oblique muscle, avoiding its dislocation from its original location and proportioning its positioning near the macular area. No references are made to methods to hermetically seal it to the sclera or to the targeted tissue. Moreover, the design of those devices does not accommodate methods to carry more than one agent, as in a bi-compartmental reservoir of the present invention described below, neither does it disclose refilling ports such as those of the present invention described herein to allow refilling or recharging of the liquid therapeutic agents.

The prior art, albeit providing methods to improve and sustain the drug delivery from an implantation site, does not recognize the need of sealing the drug delivery reservoir to the targeted tissue. Therefore, if highly cytotoxic agents are used, as are required for the treatment of intraocular retinoblastoma, exposure of surrounding tissues such as the optic nerve and extraocular muscles to the delivered agents can lead to unacceptable toxicity and limit the use of important drugs shown in vitro to be efficacious against that condition.

Slow release technologies provide control over the availability of the drug to the tissue and can prolong its therapeutic life. The present invention does not exclude the use of slow drug-release technologies. Instead, they can be incorporated as a way to improve the pharmacokinetics of agents selectively delivered to targeted tissues.

Over the past decades significant experience with periocular implants has been achieved through the established practice of encircling the eye to treat retinal detachment and by the wide use of filtration devices for the surgical therapy of glaucoma. Many polymers were tested for that purpose, and the experience accumulated over the years showed that encapsulation of the implant invariably occurs after periocular implantation. Indeed, even for largely used biocompatible medical products such as silicone, it was shown that the encapsulation process starts as soon as 3 days following insertion.(2-8) A fibrotic reaction to a prosthesis or to an structural implant is not so harmful. Instead, it may be even desired to provide mechanical stability to the implant and enhance its structural function. Nevertheless, the fibrotic reaction can lead to the extrusion of the implant from the orbit. To address that problem, adhesives have been proposed as a component of the present invention described herein to enhance implant stability.(9-11) In the case of buckling elements, adhesives can be applied to the surface of the implant in contact with the sclera, in addition to the conventional sutures placed to anchor the implant to the eyeball. Ricci and Ricci demonstrated good compatibility of buckling implants in apposition to the sclera using a cyanoacrylate derivative.(12) Cyanoacrylate has been approved for human use as tissue adhesive, n-Butyl-2-Cyanoacrylate monomer, (Indermil™ Tissue Adhesive, Tyco Healthcare Group, LP, Norwalk, Conn.). The biocompatibility and safety of derivatives of cyanoacrylate also permitted its approval to embolize malformed blood vessels after injection through a catheter, n-Butyl Cyanoacrylate (TRUFILL®, Cordis Neurovascular, Inc., Miami Lakes, Fla.).

As for buckling elements, drug delivery devices need to be anchored in place. Olsen et al., studying a device positioned in contact with the sclera, but not anchored or sealed to the scleral surface, but only positioned between the extraocular muscle and the sclera, encountered moderate migration of the device from its original site of implantation in 9 out of 9 implanted eyes.(13) Yaacobi et al. demonstrated that by implanting non-anchored or attached devices, a fibrous capsule and minimal inflammation could be found histologically. (14)

The Need For A Sealed Junction: If the possibility exists of drug leakage into surrounding tissue via a non-sealed device-tissue junction then this fact excludes the possible use of some important therapeutic agents.

The lack of a way to seal the device to the tissue would not only affect the way the stability and release profile of the active agent from its formulation, but it would also allow immunoglobulins, albumin, inflammatory cells and other components of plasma to interfere with the agent's availability and stability profiles. In addition, encapsulation of such system resulting from scar tissue formation between the drug reservoir and the organ surface could significantly change the pattern of drug release by altering important determinants of diffusion through the membrane surface, such as thickness and porosity of the membrane. The interposition of a second membrane, i.e. a fibrous capsule, between the drug reservoir and the targeted surface may also result in different diffusion coefficient since inflammatory membranes do not present the same porous characteristics as the sclera.(15) To overcome this problem, the use of an adhesive in the present invention represents a viable alternative to create a liquid-tight seal between the drug delivery device and the targeted surface.

In view of the aforementioned, there is a need for an invention that can improve the efficacy, tolerability and effectiveness of locally administered therapeutic agents. There is also a need for a method of administration that can sustain stability, delivery and effect, and control toxicity of therapeutic agents delivered thereby. The present invention, described herein achieves the forgoing goals, and can also expand the applicability of therapeutic agents that have been abandoned or had limited clinical use. In addition, the present invention can provide a stable and controlled environment where both delivery of new drugs and technologies of sustained drug release can be improved.

MORE DETAILED DESCRIPTION OF EMBODIMENTS OF THE PRESENT INVENTION

The present invention may be more readily understood by reference to the following Figures and more detailed description thereof.

BRIEF DESCRIPTION OF THE DRAWINGS

FIG. 16. Schematic view of the device implanted onto an eye surface. A refilling port, herein drum, is further connected to said device reservoir and implanted into a site of easy access.

FIG. 17. Illustrative drawing of connecting valve composed of two dishes designed to engage the edges of the refill port (hole). The valve is hollow to allow the passage of solutions injected therein.

FIG. 18. Schematic representation of refill port, represented by a drum implanted distally from the original medical device site, being approached by a refill or recharge instrument.

FIG. 21. Bottom view corresponding to the FIG. 20, where the sealing base surface is maintained constant by extending its internal edge toward the center of the release port.

FIG. 22. Illustrative drawing of the medical device with an internally extended sealing base. The radius of the sealing base of 8.53 mm was chosen to fit the surface of an eye with an axial diameter of 17 mm.

FIG. 40. Schematic view of positive solid designed to fit a device reservoir.

FIG. 41. Drawing representing dimensional relations between the several components of the system. Design to fit an eye with 21 mm of diameter.

FIG. 43. Illustrative drawing representing assembled device of FIGS. 43 and 44.

FIG. 44. Dimensional drawings of an alternative design to fit an eye with 17 mm of diameter, which represents approximately the axial diameter of a newborn eye. The final volume is 0.1 cc.

FIG. 45. Illustrative drawing of device assembled with the refill valve.

In an embodiment, the present invention comprises a medical device that is aimed to deliver therapeutic agents to organs and tissues. Said device is composed of a reservoir, which contains the therapeutic agent and its formulation or carrier polymer. The reservoir is delineated by a layer or wall on its outer aspect, wherein such wall is substantially impermeable to the therapeutic agent. On its inner aspect, which relates to the targeted tissue, the reservoir is delineated by the release port, wherein such release port can be an opening or further comprise a layer or membrane of material substantially permeable to said therapeutic agent. Said release port is delineated in its perimeter by a sealing base, which will provide a surface for sealing of said medical device to the targeted tissue. Further methods and embodiments to accomplish a water-tight tissue seal are also disclosed herein. In alternative embodiments, the medical device can also contain a refill port to allow substantial refilling of the reservoir with therapeutic agents, and a hollow tube connecting the refill port to the reservoir. Also included in the present inventions are methods for the use of the refilling port and the hollow tube and for making the device and parts thereof.

In an embodiment, said device comprises a reservoir which contains a therapeutic or diagnostic agent. The definition of "therapeutic agent" as used herein, includes, for example: compounds and compositions recognized in the official United States Pharmacopoeia, the official Homeopathic Pharmacopoeia of the United States, or the official National Formulary, or any supplement of any of them; compounds and compositions intended for use in the diagnosis, cure, mitigation, treatment, or prevention of disease in mammals including humans and other vertebrates; and compounds and compositions intended to affect the structure or any function of the body of mammals and other vertebrates.

Figure 1:
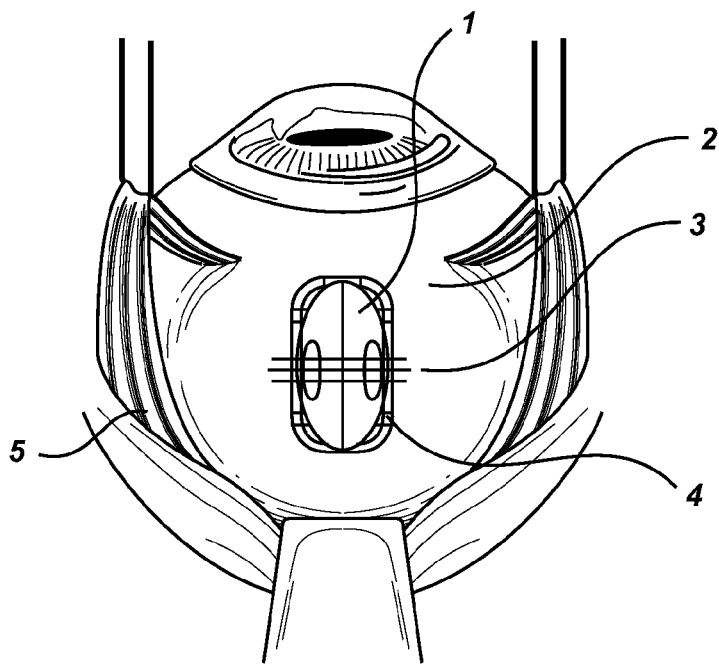
FIG. 1. Illustrative drawing of medical device 1 attached to the ocular sclera 2. The lines 3 represent sutures to create a buckle around the device and improve the sealing function of its base 4 to the scleral surface 2.

With reference to the Figures and in particular FIG. 1, a medical device 1 of the present invention can be applied to the bared scleral surface 2 after a conjuctiva excision dissection of the Tenon tissue. The strips lifted apart from the eye ball represent the extraocular muscles 5. Depending upon the size of the medical device, it can extend beyond the limits of the extraocular muscles in order to cover a larger area of the sclera. If so, flanges on its surface can be designed to allow an anatomical fit of the muscles and prevent excessive muscle and device abrasion and trauma. In the present case, the device 1 was easily positioned between muscles and sutured with a biocompatible non-dissolvable suture 3. The overlying layers of tissues are closed using standard conjunctiva suturing techniques. Numerous variations of the technique are possible. The device could be implanted in the posterior pole of the eye and the sclera end of the sutures fixed in the anterior sclera. Other methods of sealing such device to the sclera are available and can improve the clinical use of the present invention. Encircling bands as used for the treatment of retinal detachment can be passed underneath the lifted muscles and engage the medical device on its top, against the sclera. For such application, however, a slight modification of the flanges is needed to fit the silicone band. The simplest method of sealing, however, constitute the use of adhesive between the contact surface of the sealing base and the bared sclera.

Figure 2:
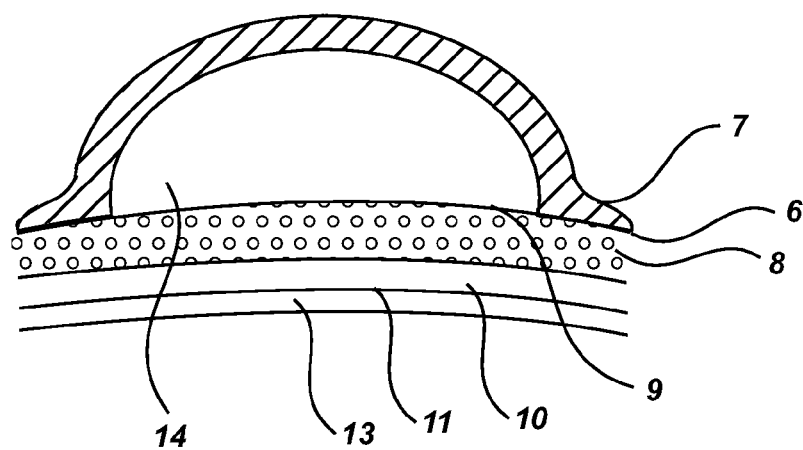
FIG. 2. Illustrative drawing of a sectioned device in apposition to the targeted scleral surface. Histologic details are represented herein.

In addition to the sutures 3 used in FIG. 1, to accomplish such sealing properties, an adhesive layer 6 between the contact area of its sealing base 7 and the sclera 8 is used herein. As demonstrated by the FIG. 2, drug diffusion will occur through the release port 9 to the sclera 8, reaching the choroid 10, retinal pigment epithelium 11, retina 12 and vitreous 13. The junction between said sealing base 7 and sclera 8 is liquid-tight to avoid leakage of the contents of the reservoir 14 to the periocular tissues.

Figure 3:
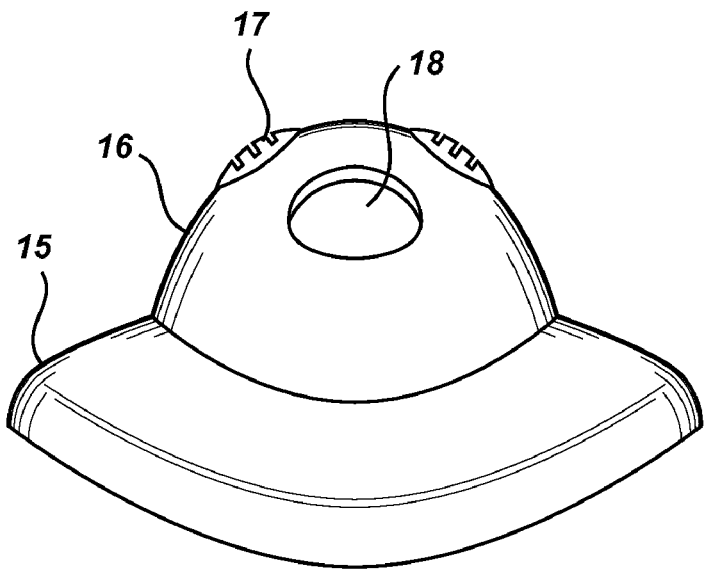
FIG. 3. Illustrative representation of the device's front view. A hole is present to allow fill of said reservoir with the therapeutic agent and its formulation. This will constitute the refill port.

FIG. 3 illustrates a device of the present invention composed of sealing base 15, which extends beyond the reservoir wall 16. As seen herein, the sealing base 15 is exposed on its external surface or non-contact surface. The reservoir wall presents suture stabilizers 17 to guarantee that once sutures are tied to buckle the device, the pressure exerted on the device will not slip backwards or upwards. The front part of said reservoir wall presents the so said refill port 18, which herein is represented by a hole. The hole 18 will be further fitted by a valve, septum or tube to allow fill of the reservoir with the therapeutic agent and its formulation.

Figure 4:
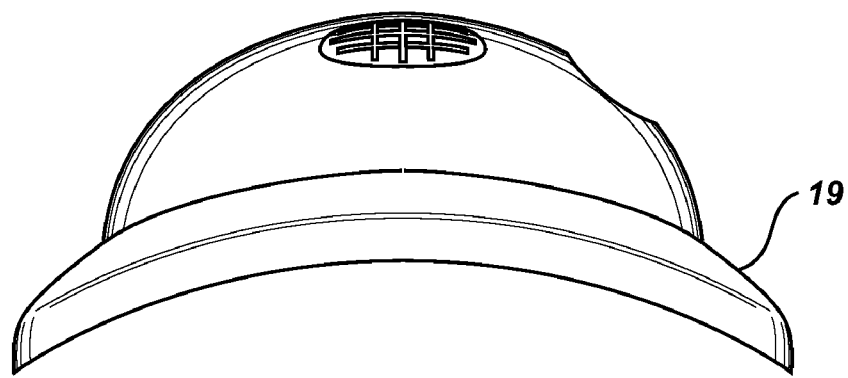
FIG. 4. Side view of the medical device.

In FIG. 4, wherein the device has the shape of a hat, the brim 19 of the hat, representing the sealing base 19, is designed to fit the curvature of the receiving (targeted) tissue. Several variations of this design are possible depending upon the volume of the carried formulation and anatomical details of the targeted tissue. The sealing base is important to accomplish seal effect between the device and the targeted tissue. In this example, the thickness of the reservoir wall is 0.4 mm.

Figure 5:
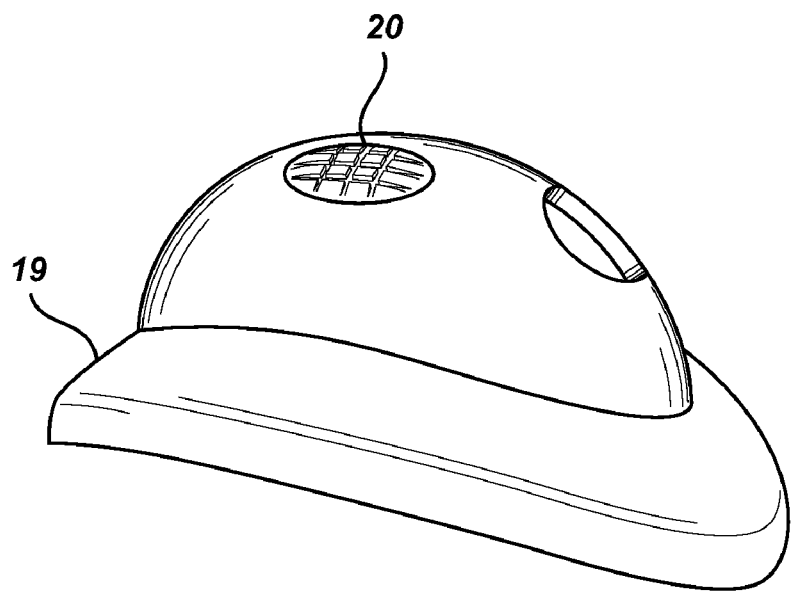
FIG. 5. Angle view of the device showed in FIGS. 3 and 4.

The FIGS. 3, 4 and 5 demonstrate that the curvature of the tissue where the implant will be attached is instrumental in designing the curvature of the implant, particularly of its sealing base. In this example, the curvature was taken into consideration based on the diameter of the infant eye, approximately 17 mm. Because the eye growth is accelerated in the first two years of life, the consistency of the material, reflected by durometer and elongation parameters, is essential in allowing accommodation of the device to the growing eye. As seen in these examples, a slightly more curved implant than the eye, and vice-versa, may not represent a problem if a mildly flexible material is used. In that case, once the sutures are positioned buckling the center of the device, the device curvature will be accommodated to the eye curvature. To do not create folds in the center of the implant where the epicenter 20 of the suture pressure will be located, reinforcement of the center can be used. Alternatively, an internal layer of solid material such as a metal can be incorporated and coated by a biocompatible polymer if necessary.

Figure 6:
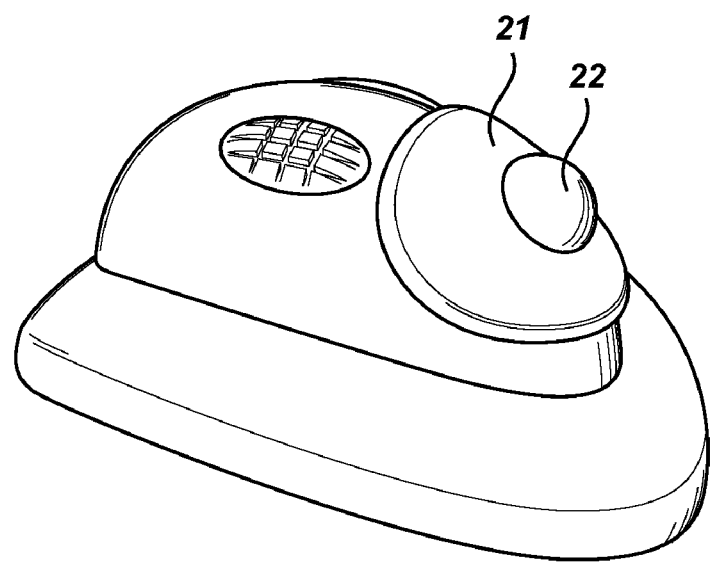
FIG. 6. Angled view of the medical device composed of a reservoir, sealing base, suture stabilizers and a refill valve in place.

The refill valve 21 in FIG. 6 fits the hole in FIGS. 3, 4 and 5. It is preferentially made of self-sealing materials such as silicone elastomer, synthetic rubber and latex. In this specific case, silicone elastomer with durometer 30 was used. The valve is designed to allow safe plunge and withdraw of the needle or refill instrument into the reservoir. A dome 22 is built on its external surface to allow recognition of the true hole diameter. It is also designed to allow identification of the valve after the device is covered by the surrounding tissue in the implantation site.

Figure 7:
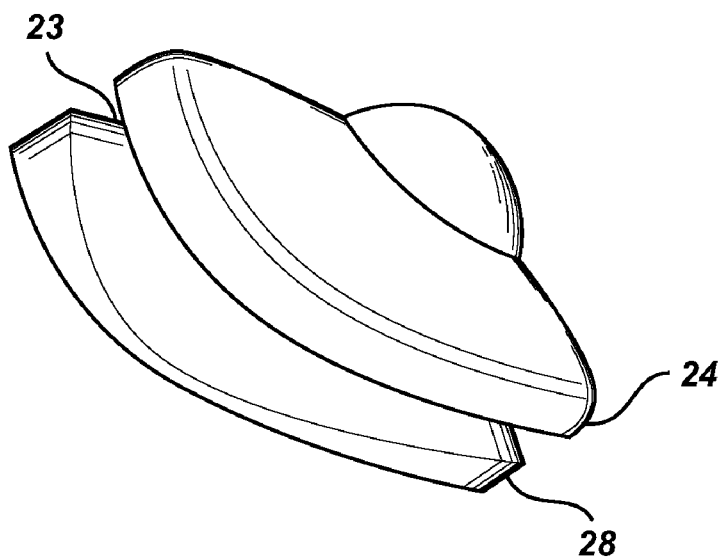
FIG. 7. Magnified view of the composed refill valve. It is composed by an external dome-shaped protuberance, two peripheral flat dishes and a central core, which is not apparent in this drawing.

The illustration of FIG. 7 shows one of the means to allow secure engagement of said valve to the refill port. The embodiment herein is composed of a central core 23, which fits the true hole corresponding to the refill port. The flat dishes 24 and 25 are attached to the central core and designed to allow a sandwich-like apposition of the reservoir wall. Once it is glued, engaged or scrolled to the refill port, it will allow safe stability under an acceptable pressure caused by the injection procedure. The need of a second dish 25 is justified by the forces applied outwards when the needle is withdrawn. Such design prevents internal and external dislocation of the refilling valve. Alternative designs are possible given the nature of the materials to be used and design of the refilling devices. For example, the stability dishes can be built from the same material or an extension of the reservoir wall, wherein a septum of a self-sealing material would be fitted in.

Figure 8:
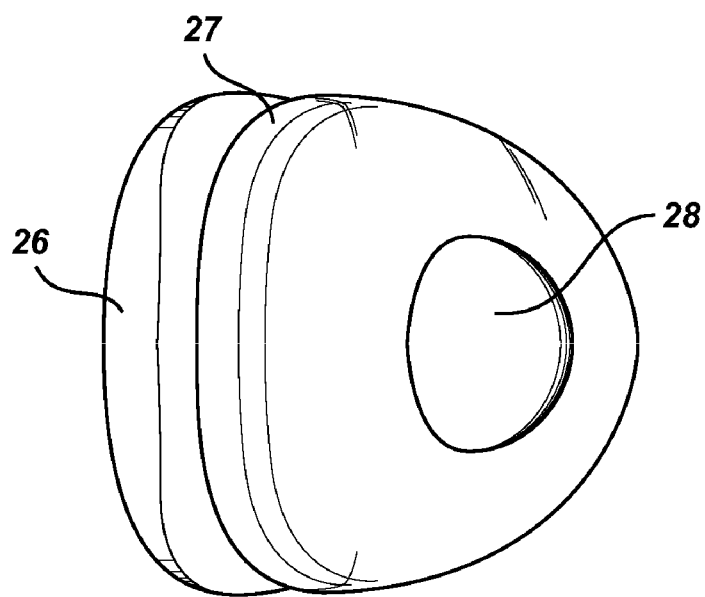
FIG. 8. Magnified view of the refill valve.

The illustration of the FIG. 8 gives a perspective of the relation between flat dishes 26 and 27, refill dome 28 and unapparent central core. The dome corresponds to an external prolapse of said central core. The diameter of the dome 28 can match the diameter of central core to allow recognition during the injection procedure of the true port hole. In addition, other methods for recognition can be used such as staining. Optimally, the flat dishes 26 and 27, follow the curvature of the reservoir wall to allow a better and secure engagement of the valve by the reservoir wall.

Figure 9:
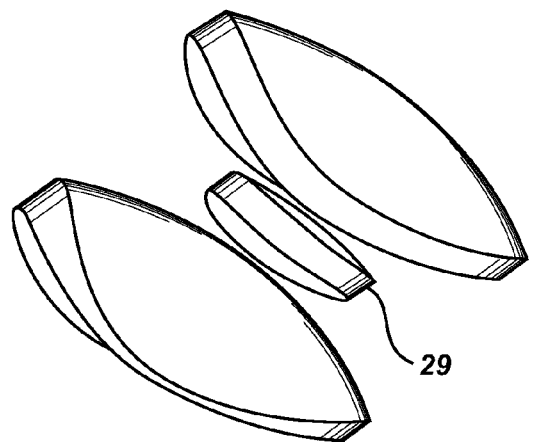
FIG. 9. Exploded view of the components of the refill valve.

The FIG. 9 illustrates the valve in its internal details. As seen here, the central core 29 is exposed and reflects the part of the valve that will be fitting the hole in said reservoir wall.

Figure 10:
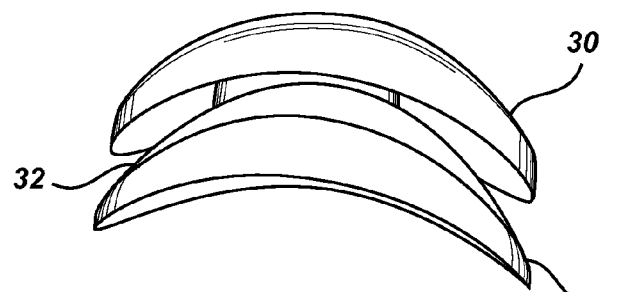
FIG. 10. Lateral view of composed refill valve.

The FIG. 10 illustrates the relations between flat dishes 30 and 31 and said reservoir wall. The space 32 between the dishes is aimed to entrap and engage the reservoir wall. Ideally it should correspond to the thickness of said wall, but if additional layers of adhesive or material are used to assembling the valve to the medical device, a slightly larger space may be required.

Figure 11:
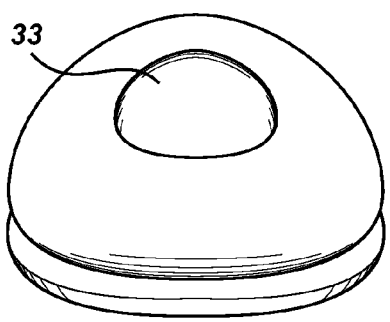
FIG. 11. Superior view of refill valve showing dome-shaped protuberance on its external surface corresponding to the true hole diameter.

The FIG. 11 illustrates the a dome-shaped 33 protuberance outwards the external surface of the refill valve. The protuberance 33 is a continuation of the central core 29 and can be used for both identification of the true port diameter as well as to facilitate visual and tactile recognition of the refill port.

Figure 12:
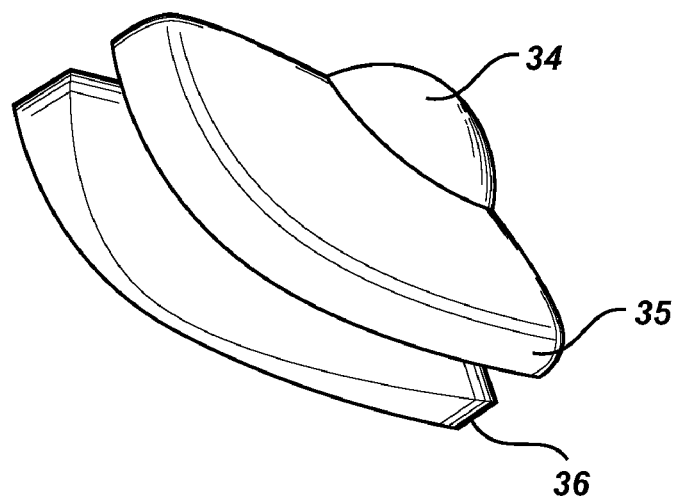
FIG. 12. Lateral view of refill valve presenting a dome-shaped protuberance on its external surface.

The FIG. 12 illustrates the side view of the refill valve presenting a dome-shaped protuberance 34 on its external surface. As seen here, the dome is created by extension of the valve core outwards with a higher curvature than the curvature of the flat dishes. The dome can correspond to the central core of the valve as demonstrated herein. Alternatively, the dome 34 can extend for the whole diameter of the said valve. Depending upon the relation between the flat dishes 35 and 36 and the reservoir wall, additional methods for recognition of the port or hole therein can be applied.

Figure 13:
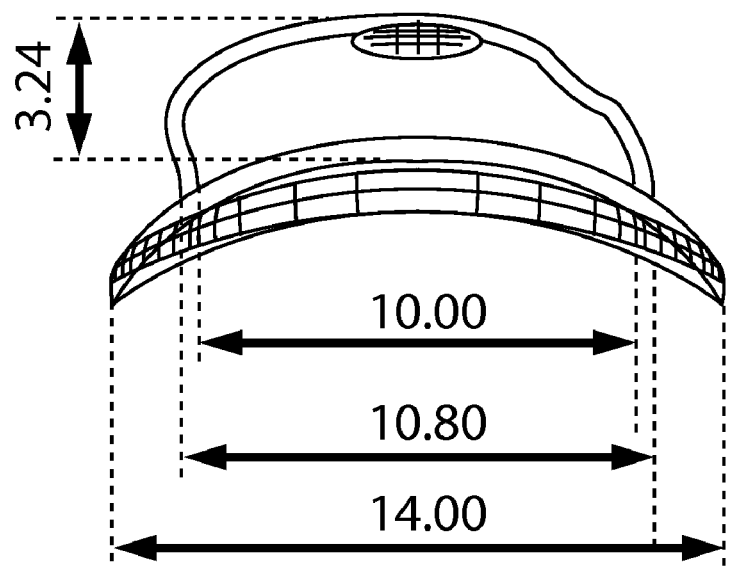
FIG. 13. Schematic lateral view of a device designed to be implanted longitudinally in relation to the axial diameter of the eye.

The FIG. 13 illustrates a variation in the reservoir design to allow a larger volume. Herein, the anterior wall of said reservoir is less curved than the posterior aspect of the reservoir. Such design allows better fit of the device onto the eye given the anatomy of the human orbit and its relations with the moving eye. In this case, the smooth anterior curvature provides more comfort and tolerance under the normal mobility of the eye. The more curved posterior edge is less susceptible to the same problem given there is more availability of space and periocular soft tissue in the posterior part of the orbit. In addition, it improves the volume capabilities of the reservoir.

Figure 14:
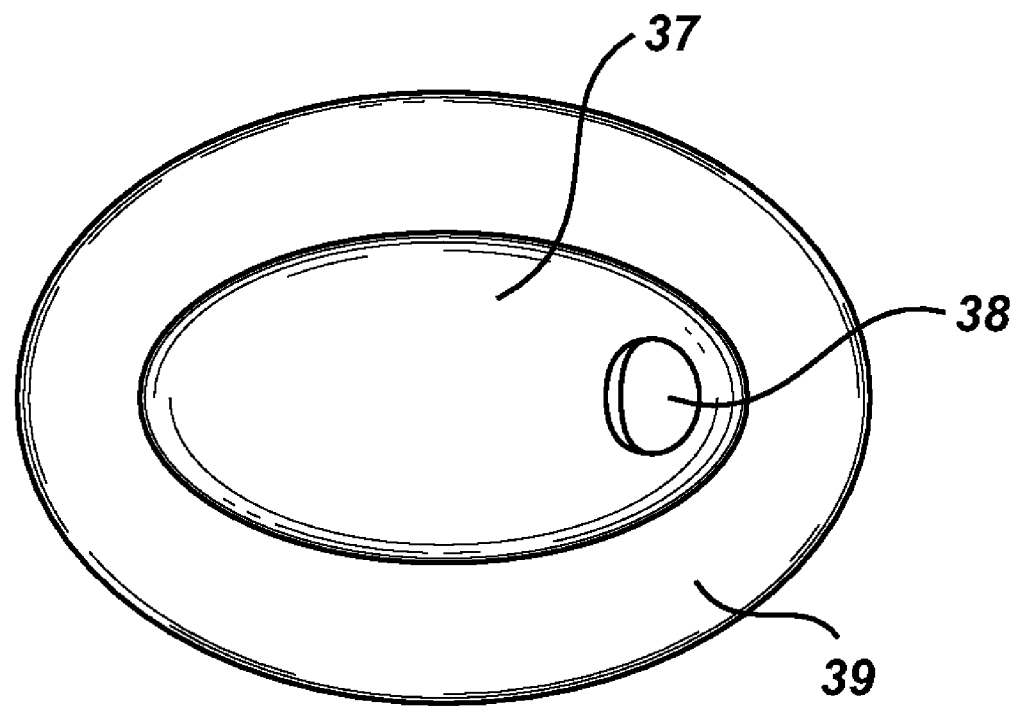
FIG. 14. Bottom view of medical device showing relations between the refill port, reservoir and sealing base.

The FIG. 14 illustrates the access to the reservoir space 37 through the refill port 38. The sealing base 39 is also demonstrated herein. The bottom or contact surface of the sealing base as exposed herein can be covered by an adhesive layer. The opening of said reservoir 37, or release port, can be fitted by a membrane to allow sustainability of liquid and solid contents inside the reservoir. In this example, the release port exposes directly the reservoir.

Figure 15:
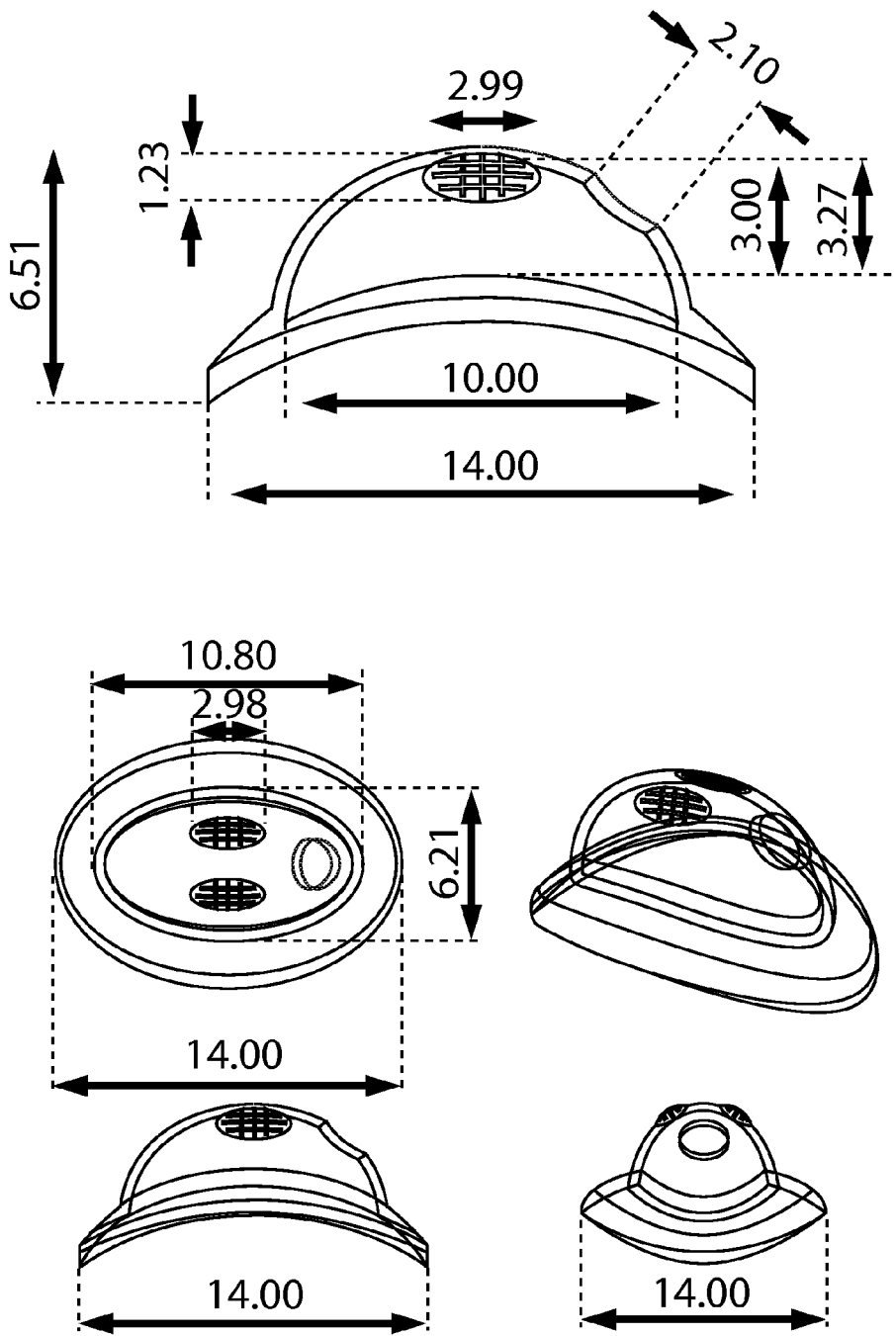
FIG. 15. Illustrative volume-oriented measures of the medical device.

The FIG. 15 demonstrates an example of integrated measures of the device to provide a final volume of approximately volume of 0.1 cc after implantation onto the curvature of an eye with a axial diameter of 21 mm. In this case, the largest diameter of the release port is 10 mm. Given the width of the sealing base, 2 mm, the largest diameter of the medical device is 14 mm. The smallest diameter, or width of the release port is 6.21 mm and of the medical device is 10 mm. As demonstrated in this example, the maximum height of the device is 0.327 mm from the targeted surface where the device is implanted. Variations from these measures are possible are exemplified thereinafter.

The FIG. 16 illustrates a medical device composed of a sealing base 40, suture stabilizers 41, refilling port 42, connecting tube 43 and drum 44, The refill port 42 herein is composed of a drum 44, which is implanted in a site where it can be easily accessed by a refill instrument. As an example, the drum 44 is implanted anterior to the equator of the eye while the device is located posterior to the equator. The drum can be further covered by a scleral graft to improve its tolerance under the conjunctiva.

The valve in FIG. 17 is composed of two flat dishes 45 and 46, which will allow a secure attachment to said reservoir wall as for the refill valve. The protruding parts 47 and 48 from the dishes permit attachment or engagement of the hollow tube or a catheter after projection into its lumen. Methods for engagement of said protruding parts by hollow tubes include mechanical engagement, adhesive and heat assisted attachment and scrolling. Alternatively, they can be molded altogether.

The contact surface of said drum 49 is not apparent in FIG. 18. It follows the same curvature of the implanted tissue surface. Its external surface 50 is designed to avoid sharp edges yet permitting visual recognition. In addition to visual recognition, other methods can be used are referred for said refill valve. At least of its surfaces can be injected or perforated by a refill or recharge instrument 51. In this case, the drum has 4 surfaces, the outer 50, which is convex, inner, which is concave 52 to fit the curvature of the eye, a posterior 53, connecting to the hollow tube, and anterior 54, flat herein to be perforated by the instrument 51.

Figure 19:
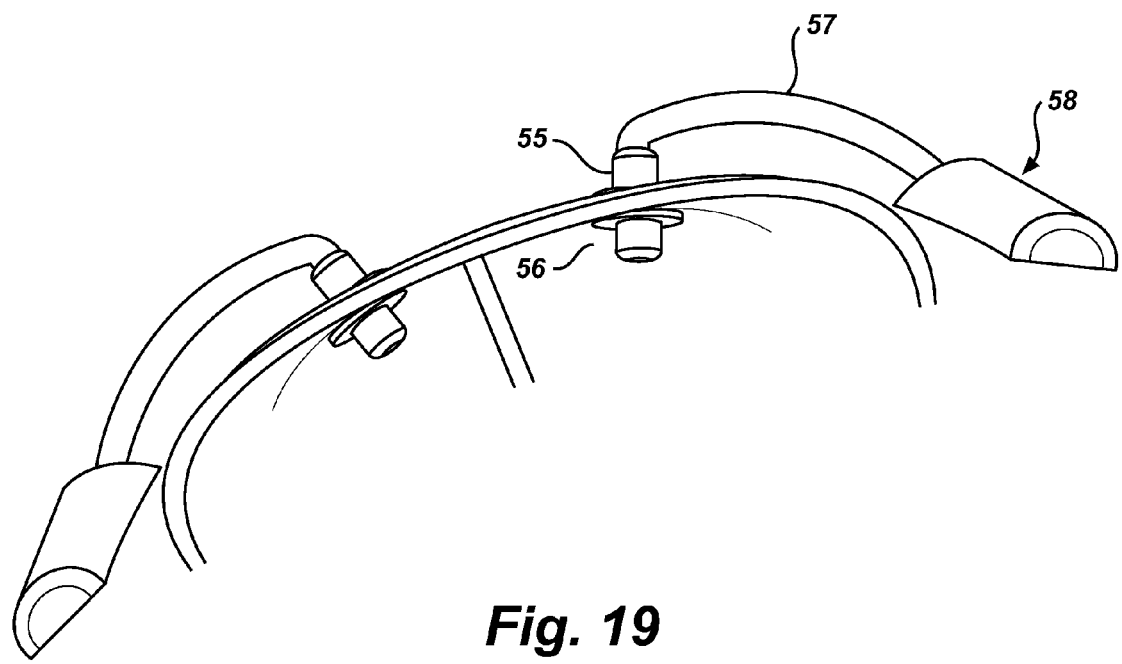
FIG. 19. Schematic view of the assembled refill parts.

In FIG. 19, details of an assembled refill system can be contemplated. A connecting valve 55 is assembled to the reservoir wall and communicates its lumen 56 to the outside of the reservoir. It further fits a hollow tube 57, which is distally connected to a refill drum 58. The drum is made in at least one of its surface of a self sealing material. Optimally the material is chosen from the class of a silicone elastomer, synthetic rubber and latex. The solution containing the therapeutic compound is injected into said drum and will refill the reservoir. The drum is elastic to allow accommodation of the injected volume before it permeates the reservoir. The volume of the drum should optimally correspond to 0.1-10% of the volume of the reservoir. Before refilling the reservoir aspiration of the drum 58 and therefore, of the volume contained in the reservoir may be required. Other embodiments are discussed in the detailed description of the invention.

Figure 20:
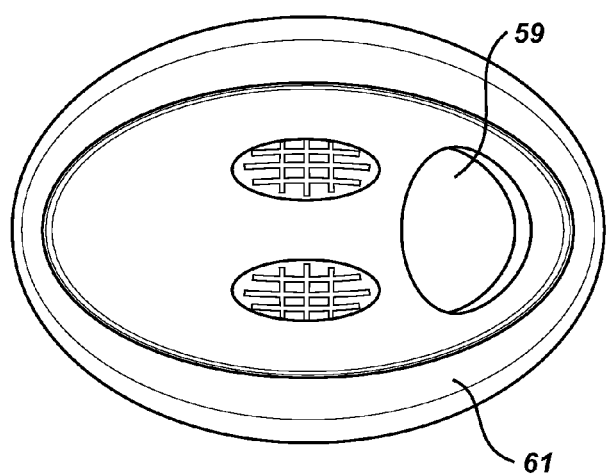
FIG. 20. Top view of device with an enlarged refill port and reduced diameter. Design variations were applied to reduce the overall dimensions of the device.

The FIGS. 20 and 21 illustrate a design variation of the medical device, wherein the release port 60 is reduced in diameter to allow minimization of the device dimensions without changing the sealing base 62 area. The release port 60 area corresponds to the diffusion interface area and is an important determinant of the diffusion rate through the targeted surface. The control of the release port area represents a way to control the diffusion rate to the targeted tissue. Increasing the sealing base contact area also improves the seal of the device to the targeted tissue. Tight control over the seal is attained by the use of the sealing accessories and methods and by control over the sealing interface area 62.

The drawings in FIG. 22 show that the sealing base extends internally into the center of the release port. By doing so, the largest diameter of the device with a reservoir volume of approximately 0.1 cc is reduced to 12 mm and the smallest diameter, or width, to 8.57 mm. The reservoir extends 3.29 mm from the ocular surface on its maximum height. A refill port measuring 3.51 mm of diameter is used herein.

Figure 23:
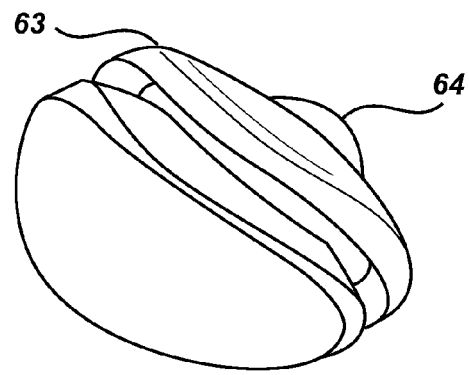
FIG. 23. Illustrative bottom-lateral view of said refill valve designed to fit a 3.5 mm wide refill port.
Figure 24:
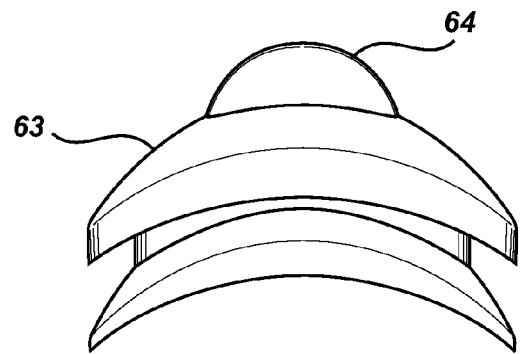
FIG. 24. Illustrative side view of refill valve showing relation between its different components.

FIGS. 23 and 24 illustrate a refill valve 63 designed to fit a large-diameter port. In these examples, the refill valve comprises a dome shaped protuberance on its center 64. Such accessory as demonstrated herein is used to facilitate identification of the refill valve 63. Variations of said protuberance are predicted and include size, shape and positioning. The protuberance can also be used and designed to orient the plunge of the refill device. As a non-limiting example, the perimeter of the central core can be composed of a rigid material and extend externally and internally to facilitate a controlled plunge of the refill device.

Figure 25:
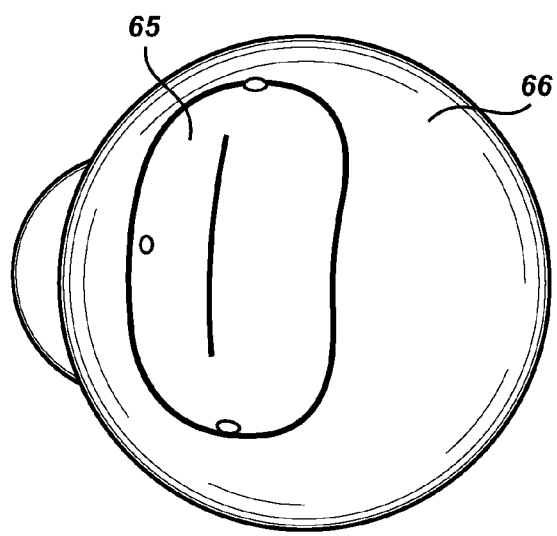
FIG. 25. Illustrative drawing representing medical device applied onto the equator of an eye.

The FIG. 25 illustrates a medical device 65 that once applied to the equator of the eye 66 can expose a large area of the sclera and underlying structures to the delivered therapeutic agent. The equator of the eye is composed internally of the most peripheral part of the retina and posterior part of the pars plana. The device can deliver high levels of a therapeutic agent to the cilliary body, which is located anterior to the equator. Those tissues are not only the sites of inflammatory processes in the eye, but the cilliary body is the tissue responsible for producing aqueous humor. Inhibition of production of aqueous humor is one of the strategies used to treat glaucoma. Agents such as carbonic anhidrase inhibitors were shown to diffuse through the sclera and can be delivered by the embodiment represented herein.

If interpositioned underneath the rectus muscles, flanges can be built to facilitate its engagement and fit beneath the muscles. Alternatively, more than one device can be applied to the same eye. The details on side of the device represent suture stabilizers, to which the stitches can secure the implant against the sclera and prevent its mobilization from the original site. Particularly if positioned underneath the rectus muscles, seal and anchoring accessories are of major importance since the rectus muscles control the movement of the eye and its movement can determine abrasion of the implant and dislocation thereof. Optimally, the implant is placed underneath the lateral rectus avoiding contact with the oblique muscles and vorticous veins of the eye.

Figure 26:
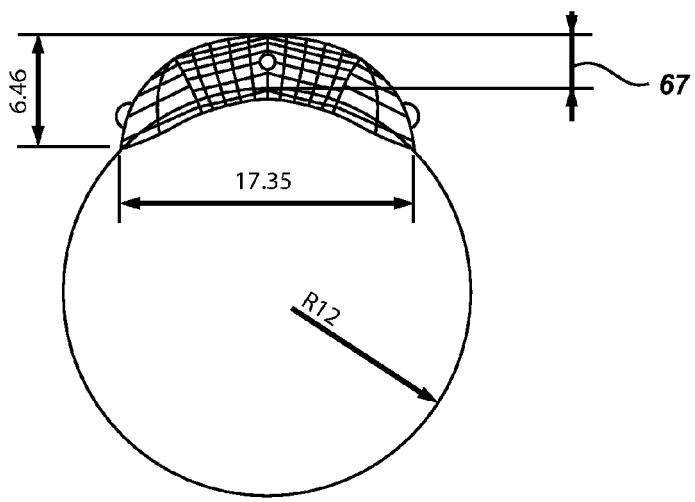
FIG. 26. Illustrative drawing of an equator-mounted device.

The reference eye represented in FIG. 26 has an axial diameter of 24 mm. The device has the largest diameter of 17.35 mm and maximum distance 67 from the scleral surface of 3.3 mm. Such design will provide a volume of approximately 0.3 cc.

Figure 27:
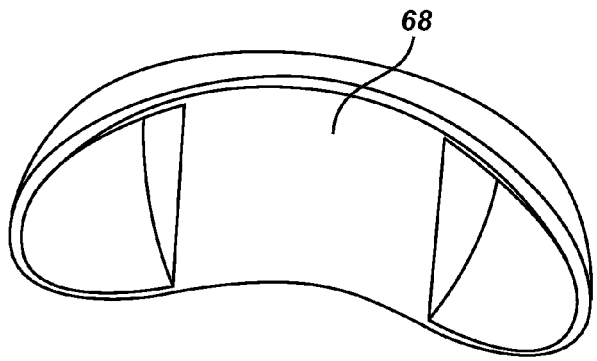
FIG. 27. Bottom view of the device reservoir. A bridge or band 68 is attached or built on the central aspect of said release port to sustain a pellet or combinations thereof positioned inside the reservoir.
Figure 29:
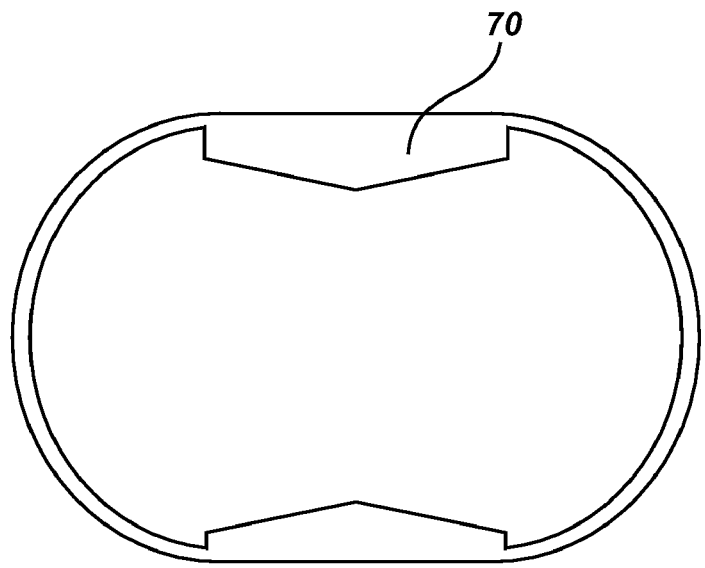
FIG. 29. Bottom view of the device release port illustrating protuberances 70 from the perimeter of the release port used for holding a solid content inside the reservoir.

The FIG. 29 illustrates non-limiting examples of methods used to hold contents inside the reservoir. The FIG. 27 illustrates a bridge 68 that is built or incorporated to the release port by means of gluing, mechanical attachment or molded as part of the device casing. Such bridge can be built at any portion of the release port. Herein it was built in across the center to allow a better stability of the solid content. The area of the bridge built therein is also determinant of the interface diffusion area. To calculate the diffusion interface one should take into consideration the area of said bridge. Alternatively, if the bridge is built in a different plain than the release port and not placed in contact to the sclera, it will not substantially affect the diffusion interface area. Elastic materials are preferentially used to make the bridge. More than one bridge can be built using different widths. Different materials can be applied or materials with different characteristics. Optimally, the bridge is more elastic and more easily elongated than the reservoir wall to allow manipulation and introduction of the solid material in the reservoir cavity.

Figure 28:
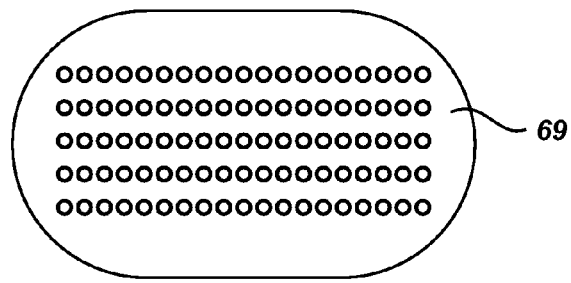
FIG. 28. Bottom view of the device release port, wherein a fenestrated membrane 69 is built to sustain a viscous or solid content inside the reservoir.

The FIG. 28 illustrates another example of methods to hold contents in the reservoir. The release port is covered by a fenestrated or porous membrane 69, which is molded with the device casing or separately. If separately, it can be incorporated to the casing by attachment using adhesives, or alternatively by mechanical engagement. Alternative methods include heating and photopolymerization. The number and diameter of fenestrations is to be determined by the characteristics of the drugs and formulations contained in the reservoir. The membrane can be built in a higher plan than the release port to do not interfere with the diffusion interface area. Other embodiments are possible. For example, the membrane can extend to the contact surface of the sealing base and constitute a first layer before the adhesive layer is applied therein. Second coating of the membrane is also possible to control the diffusion of compounds from the reservoir before the reach the targeted surface. For example, a membrane composed of EVA, or ethylene-vinyl acetate can be incorporated to the inner or outer side of the fenestrated membrane. In that case, the fenestrated membrane would also provide support to the EVA membrane.

The FIG. 29 illustrates a simpler method to hold a solid pellet or capsule inside the reservoir. It constitutes internal flanges or protrusions 70 from the edge of the release port. These protuberances can be built in any number and position along the edge of said release port. For assembling, they can be built in the same mold but using different material or thickness. For example, a protuberance of 0.1 mm built in a device with thickness of 0.4 mm will allow a relative elasticity for introduction of the pellet inside the reservoir.

The assembling of the methods illustrated by FIGS. 27, 28 and 29 should take into consideration the drugs and formulations that are carried in the reservoir. The presence of the refilling port would allow fill of the reservoir after assembling of the device. However, if solid agents are to be used, a previous fill of the reservoir with said agent might be required followed by further assembling of the device, packaging and sterilization.

Figure 30:
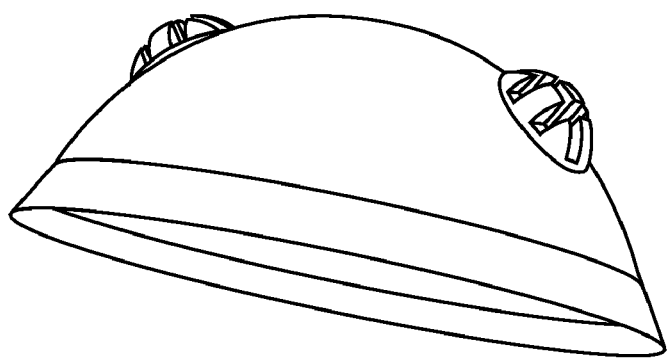
FIG. 30. Side view of spherical medical device.
Figure 31:
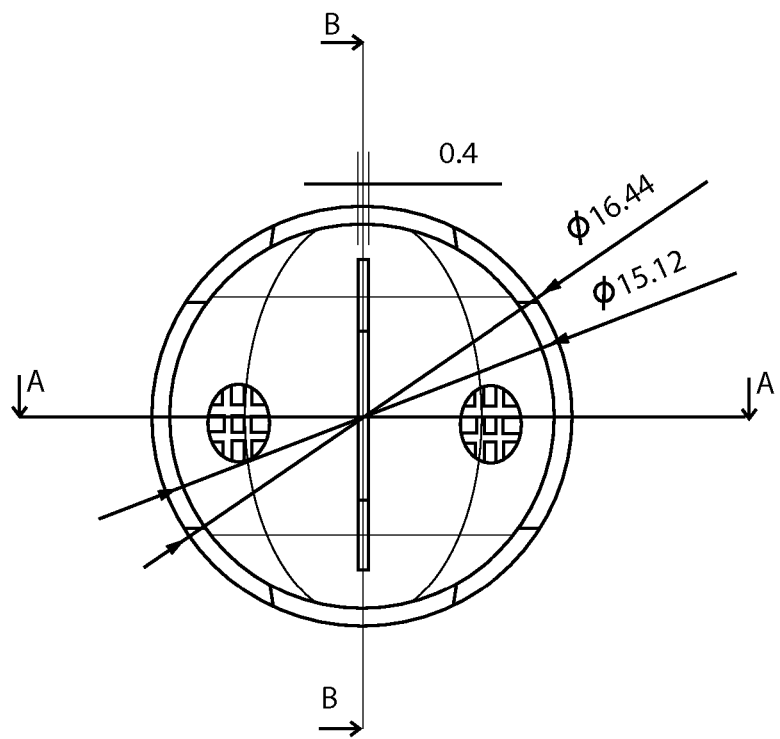
FIG. 31. Schematic superior view of spherical medical device showing device external diameters. The overall diameter is 16.44 mm and the reservoir diameter is 15.12 mm.
Figure 32:
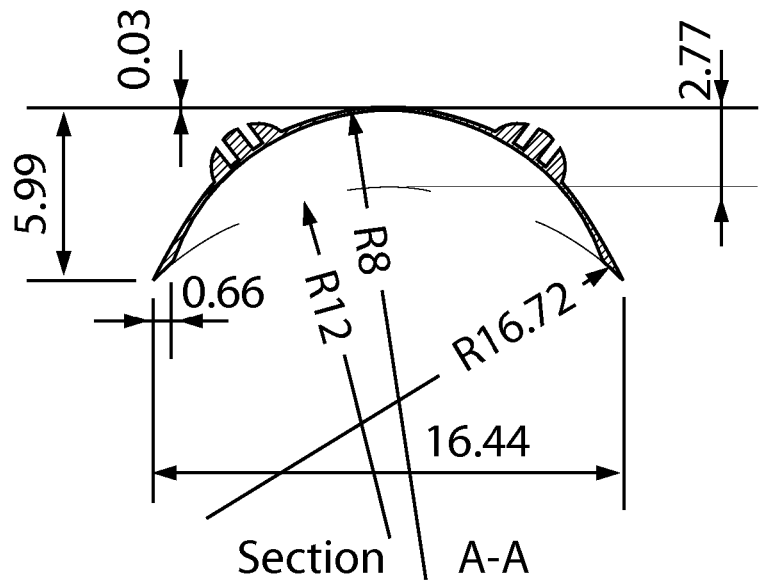
FIG. 32. Schematic view of medical device showing relations between different parts and curvatures of the device.
Figure 33:
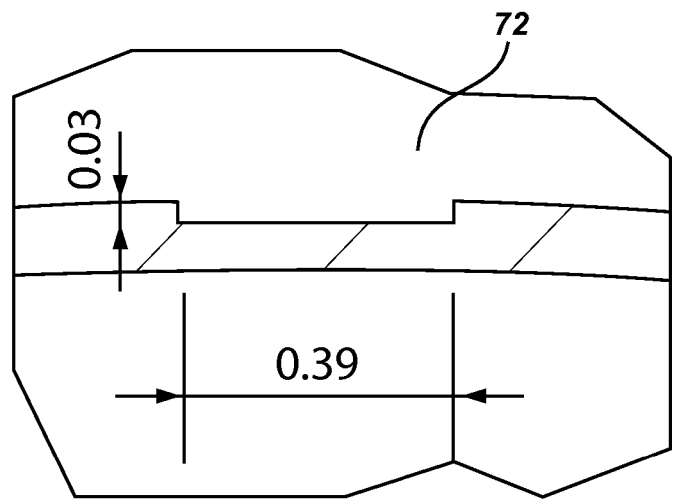
FIG. 33. Details of the groove built onto the outer surface of the reservoir wall.

The devices in FIGS. 30, 31 and 32 represent the different curvature parameters that can be used to construct the casing of spherical device. In this example, the radius increases towards the center of the device. The most external curvature is represented by the radius of the eye and is aimed to fit the eye surface. Then the radius increases from 12 mm to 8 mm in its most central aspect. The progressive change in the radius curvature reflects the need of creating a reservoir that is progressively more spherical to allow better tolerance once it is implanted onto a tissue. The groove 71 in FIG. 32 is designed to allow engagement of a buckle, crossing suture, or a body tissue. It can vary widely in diameter depending upon its application.

Figure 34:
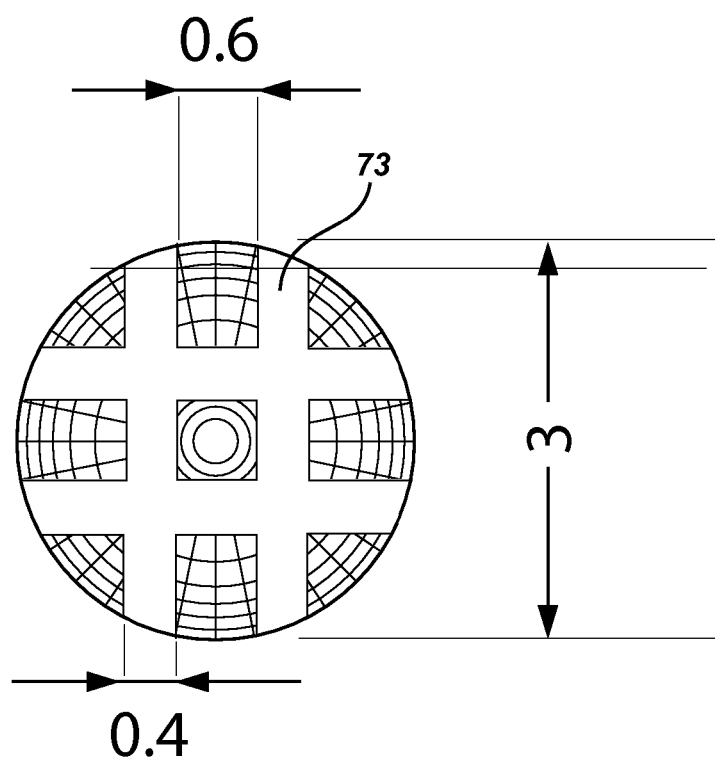
FIG. 34. Top view of the suture stabilizer. Example of dimensional details are illustrated herein.

A series of grooves 73 is built in the suture stabilizer located on the top of the device are illustrated in FIG. 34. The grooves will be further occupied by sutures and will allow stabilization of the medical device under a certain pressure after said sutures are tied up.

Design variations can be used to allow improvement of certain parameters of the device functionality.

Figure 35:
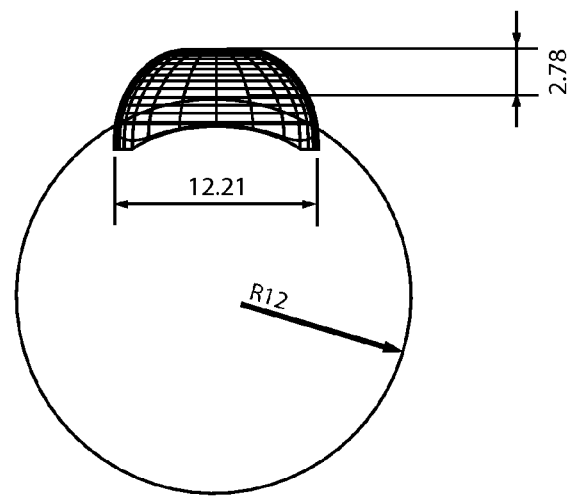
FIG. 35. Schematic posterior view of a device applied to an eye with axial diameter of 24 mm. The device herein carries a volume of 0.3 cc.
Figure 36:
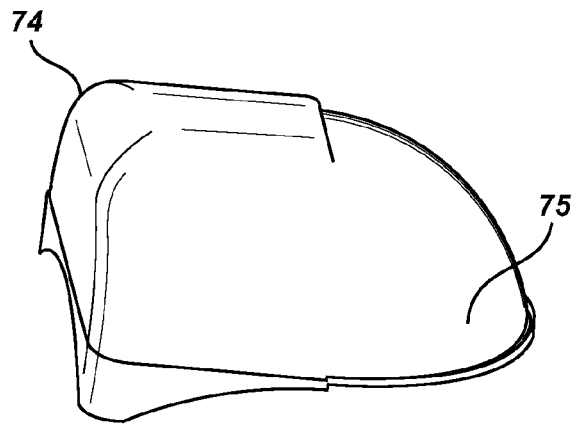
FIG. 36. Superior view of device designed to maximize the reservoir function in its posterior part.
Figure 37:
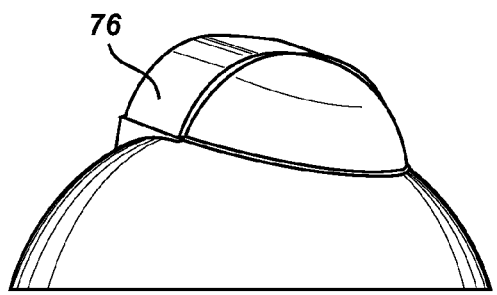
FIG. 37. Schematic view of device implanted onto a sphere surface representing the eye.

The design of the device takes into consideration the volume of the solution carried inside. To maximize the reservoir function of the device, a more squared shape 74 can be used for its posterior aspect. The devices shown in FIGS. 35, 36 and 37 have a volume of approximately 0.3 cc. Its spherical part 74 points toward the anterior part of the eye. The squared reservoir 76 is placed posteriorly where it can be accommodated by the periocular fat and soft tissue.

Figure 38:
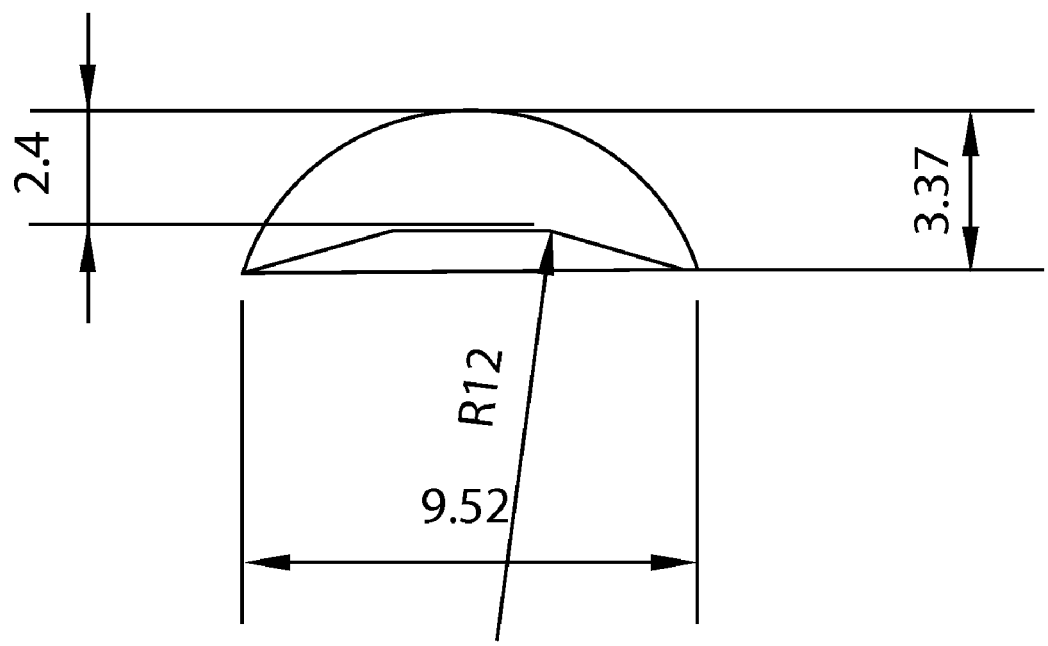
FIG. 38. Schematic drawing of device reservoir dimensions to fit onto an eye with axial diameter of 24 mm.

The dimensional calculation of the device reservoir is essential to determine the parameters for design and construction of tablets to be fitted therein. In the example of FIG. 38, the device, designed to fit an eye with axial diameter of 24 mm, has a circumferential diameter of 9.52 mm, arc length of 9.72 mm and a maximum height of 2.4 mm from the scleral surface.

Figure 39:
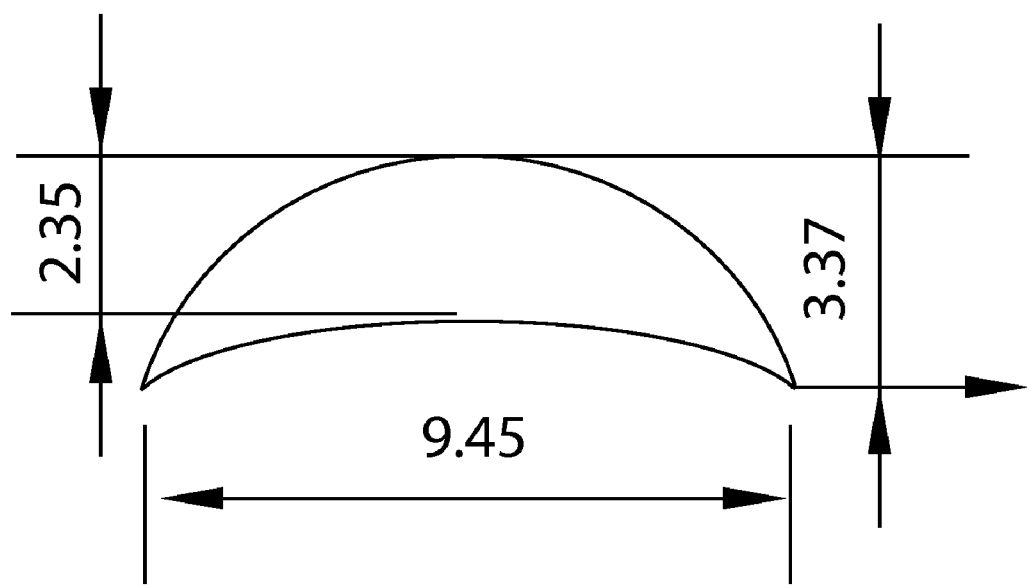
FIG. 39. Schematic drawing representing dimensions of reservoir content.

The FIGS. 39 and 40 represent the positive solid to be fitted into the reservoir of FIG. 38. The same solid can be composed of different layers containing different compounds and polymers in order to accomplish a predicted and desired drug release rate.

FIG. 41 demonstrates that the device has a sealing based that is part outside the limit of the reservoir wall and part inside. The inner edge of said sealing base represents the perimeter of the release port. Variations of these dimensions are possible depending upon the desired overall diameter of the device, release port surface area. Here the largest diameter of the device is 12 mm, largest diameter of the release port is 8.57, yet the largest diameter of the reservoir is 10 mm. The maximum height, represented by the maximum distance from the sclera to the reservoir roof is 3.33 mm. Other dimensions are represented in the drawings.

The device by FIG. 41 has a refill port, which will be fitted by a refill valve. The valve has the dimensions that fit said hole and allow a mechanical and/or adhesive attachment therein.

Figure 42:
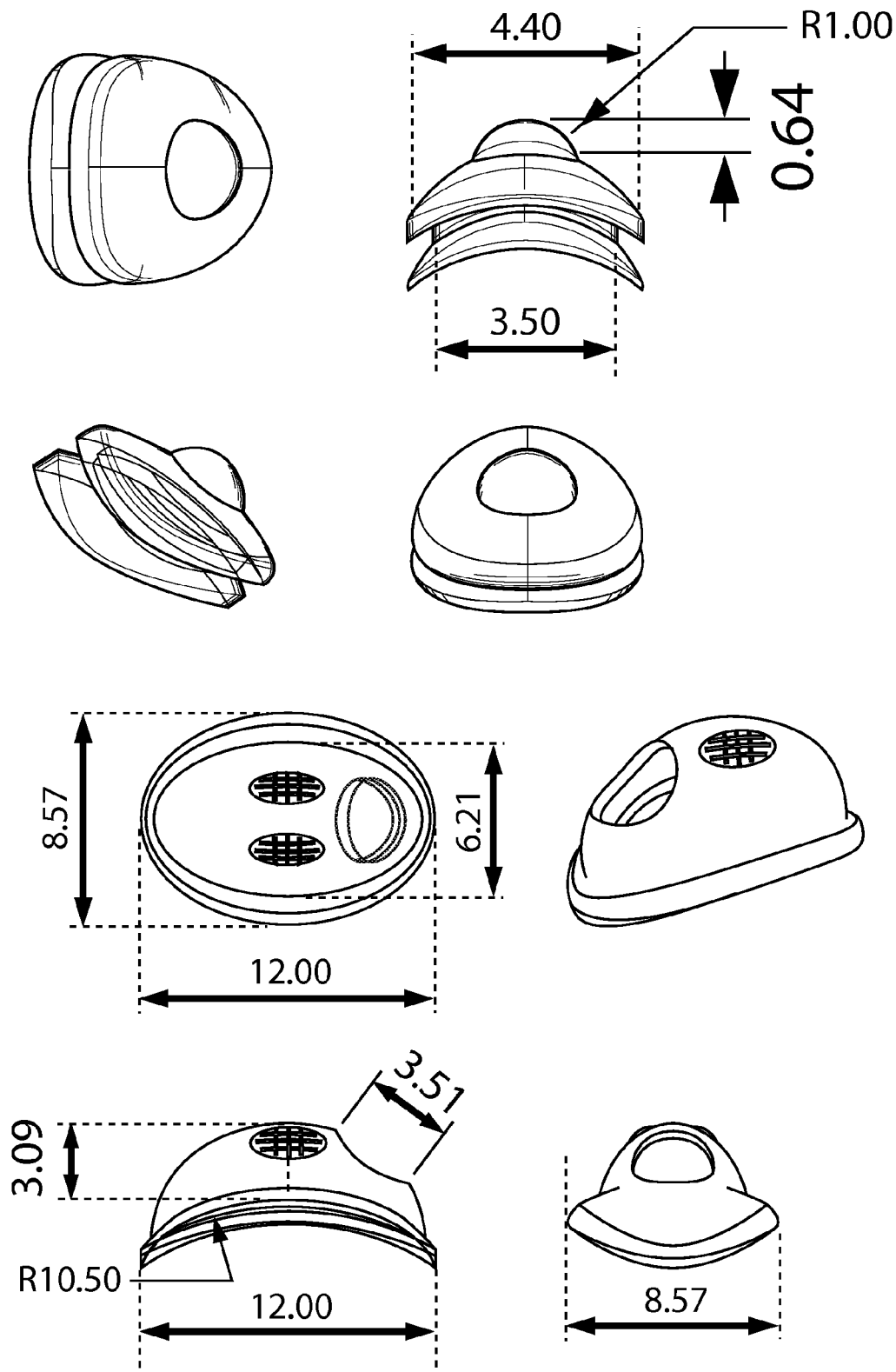
FIG. 42. Illustrative drawings of device dimensional details to accept the refill valve.

For the hole designed in the FIG. 41, the FIG. 42 demonstrates the dimensions that will be applied to the device design. In the present example the valve core will have a diameter of 3.5 mm. The overall diameter, which includes the diameter of the flat dishes is 4.4 mm. Different proportions between the parts are possible and predicted depending upon the overall device dimensions, dimensions of the refill device and methods for refill. After assembling the device will appear as shown in FIG. 43.

The FIG. 44 shown how the dimensions relates also as a function of the curvature of the receiving surface. In the case of the newborn eye, measuring 17 mm of axial diameter, the radius of 8.5 mm will determine slight changes in the design compared to the design of the FIG. 41. Alternatively, extra parameters can be added to the calculation depending upon the degree of precision needed for designing the device. An extra dimension or diameter can be added, for example the equatorial diameter of the eye, which is slightly different from the axial one, to enhance the precision of the calculation of the device parts and improve its fit on the eye surface.

The FIG. 45 demonstrates an assembled device. The refill valve protuberance 77 has the shape of a dome and occupies the whole port diameter, 3.5 mm, as demonstrated by FIG. 44.

The therapeutic and diagnostic agent can be covalently or non-covalently bound to a carrier compound to control its release rate, provide stability and/or to provide structural stability of the agent inside said reservoir.

In another embodiment of the device, the reservoir comprises an empty cavity. The empty cavity will provide space to be filled with a therapeutic agent in an appropriate time following implantation.

When the device is implanted and contains a therapeutic agent, upon release of the agent, the reservoir can be refilled or replenished with the same or different therapeutic agent. The reservoir is refilled by injection through its wall when the wall is composed of materials that are optimally flexible, elastic, and particularly self sealing or by injection into a self-sealing septum built in the reservoir wall. Said self sealing septum functions as a filling or refilling port.

In an alternative embodiment, said device comprises more than one reservoir. The wall of the reservoir comprises a refilling port, wherein said refilling port comprises a self-sealing polymer, preferentially made, but not limited to a silicone elastomer with low durometer. Said reservoir wall may comprise at least one refilling port for at least one cavity.

The self-sealing septum is made of an elastic and self-sealing material. As a non-limiting example, silicone elastomer with low durometer, preferentially with durometer between 20-50, or in an another embodiment between 10-80. Rubber and latex can also be used. The self sealing septum can be incorporated to the reservoir wall by gluing, welding, or by other suitable method. The septum is sealably connected to the reservoir to prevent leakage or dislocation during the refilling procedures and thereafter, resulting in a safe device.

An embodiment for said self-sealing septum comprises a plug, composed of a central body. The body of said plug is preferentially made of an elastic material with a larger diameter than the hole built in said reservoir wall to accomplish a better engagement of said plug by said hole. It has preferentially the same thickness of the reservoir wall, but it can be thicker than the reservoir wall to allow a better seal of the orifice created during the trajectory of the refilling device, e.g. needle. The body of said plug can extend beyond the limits of the inner and outer surfaces of the reservoir wall. In one embodiment, the desired thickness to allow seal of the port after refilling procedures can be accomplished by extending the body into the cavity of the reservoir, referred hereinafter as inner extension of the plug. In another embodiment, the body extends outwards the outer surface of the reservoir wall, named hereinafter outer extension of the plug. Preferentially, the outer extension has smooth surface to minimize chronic trauma to surrounding tissues. Said surface is rounded and slightly spherical. The outer extension can be stained with biocompatible dyes to allow better identification during the refilling procedure. It can also be radiopaque in order to be identifiable by imaging techniques. Additional methods such as the use of magnetic resonance imaging, computer tomography and ultrasound can be used to identify the refilling port, which is stained by agents opaque to the referred diagnostic and imaging methods. Methods of incorporating dyes and markers to materials are widely available by those skilled in the art and are used for identification, as example, of gauze, catheters and interventional radiology instruments.

The inner extension of said plug is preferentially built to drive the needle to a safe portion of said reservoir. As an example, if said device in implanted onto the curved surface of the eye, the convex surface of the eye should not be perforated by the needle and therefore, the degree of inclination between said plug and reservoir wall should be constructed taken into account that by plunging the needle through the reservoir, said needle, or refilling device, should not encounter the scleral tissue on its way to the opposite side of the reservoir wall. And that depending on the position of the plug and refilling port in said reservoir wall, the angle between the plug and the reservoir wall optimally should be different than 90 degrees. Preferentially, the angle should be between 45 and 90 degrees so as not to interfere with the refilling procedure.

The plug is preferentially placed and directed toward a point in the opposite reservoir wall in order to avoid perforation of the tissue-targeted surface. Alternatively, it can point toward the center of the reservoir and methods to avoid perforation of the tissue can be applied. Such methods can be applied to the needle design. As an example it may include a stop point, elevation or sign on the needle surface, which limits further progression of the needle into the reservoir. If two needles are used, the first for injection and the second for aspiration, a bridge can be built between them, wherein said bridge will be placed and function as a limiting obstacle to excessive penetration of the needles into the cavity. If a plug is built directed to the targeted surface, the refilling instrument could provide features to accomplish safe insertion and conduction of the procedure. Such features include but are not limited to changing the curvature of said refilling instrument, incorporation of a stop point on the outer surface of such instrument and, therefore preventing penetration beyond a certain extent. Designing instruments with safe devices to prevent misplacement and erroneous perforation of tissues is well known by manufacturers of needle and catheters. Several variations exist and can be applied herein.

In another embodiment said plug is composed of a body and at least one flat dish. Preferentially, two flat dishes are incorporated wherein an outer flat dish is in contact with the outer surface of the reservoir wall and the inner flat dish is in apposition to the inner side of the reservoir wall. Said dishes aim to provide a better stability to the plug in the reservoir wall, avoiding its dislocation during refilling procedures and improving its seal to the reservoir wall. In providing stability, the outer dish aims to avoid internal dislocation of the plug into the reservoir, during the injection procedure, and the inner dish aims to avoid dislocation to the outside during the withdrawal of the injection device. Said dishes can be attached to the plug core and to said reservoir wall by apposition, gluing and scrolling. Preferentially, however, they are molded and made altogether. To build said dishes on both sides of the plug one should take into consideration the method that will be used to attach them to the reservoir. If a thick layer of a silicone adhesive is to be used, space for interposition of such layer should be provided.

An embodiment of the present invention can comprise an extension of said refilling port from the reservoir wall. A hole can be built into said reservoir wall. Said reservoir wall extends outwards or inwards from the reservoir wall to form a protuberance. Said protuberance comprises a self-sealing septum or can be connected to a tube preferentially by means of mechanical engagement, scrolling, chemical attachment, physical attachment or by the use of adhesives. In another embodiment, said refilling port is implanted distally and connected to the reservoir by means of a tube, which is proximally attached to an opening in the reservoir wall.

The refilling port is connected to the reservoir by a hollow tube made preferentially, but not restricted to a silicone elastomer, wherein said tube may be flexible to facilitate its implantation into or onto a site in/on a mammalian organism. Alternative flexible or inflexible materials are available to manufacture catheters and infusion lines and can be applied herein. Said hollow tube may also be made of the same material used for construction of said device. Alternatively, said tube may be made of a same material with different characteristics, and of a different material. If different materials or materials with different properties are used, different combinations of materials are possible, for example, a wall is made of a rigid silicone elastomer, and said hollow tube is made of a flexible silicone elastomer. The length of said tube may vary from 0.1 mm to 2,000 mm, depending upon the location and distance from the refilling port to the site of implantation of said reservoir.

In an example of the use of the embodiment, the device is placed in apposition to the sclera, and sealed to the sclera. The device is placed posterior to the eye, aiming to deliver drugs to the macula and adjacent tissues. To facilitate the access to the reservoir, the refilling port is placed underneath the conjunctiva, in the anterior part of the eye. The refilling port is anchored to the sclera by standard suture techniques to guarantee stability and maintenance of the original position of said refilling port. Said refilling port is connected to the reservoir by a hollow tube. In the postoperative period, given an appropriate scar formation and stability of the device is accomplished, the refilling port can be accessed by a hypodermic needle, a cannula, or a delivery device. The procedure may involve a simple trans-conjunctival or trans-dermal injection to reach the refilling port. The therapeutic agent is delivered to the hollow tube, and said therapeutic agent, by passing through said hollow tube, reaches the reservoir. The hollow tube has a length sufficient to reach from the reservoir location on the posterior of an eye to anterior refill access location.

Alternatively, the hollow tube may be divided by at least one wall, and at least one hollow tube is connected to the reservoir and to the refilling port. Said refilling port may comprise at least one site for delivery of the agent, and at least another site to allow reflux of residual solutions, or air, contained in the reservoir. In another embodiment, the refilling port may comprise a valve to allow regurgitation of excessive fluid inside the reservoir, without compromising the sealing characteristics of the device. Said valve can be alternatively built in the external wall of the device. It is preferentially made of a silicone elastomer, by incorporation to the device during or after the molding process of said reservoir.

A mechanical valve to close said opening to the reservoir and prevent overfilling is preferentially built into the opening of said reservoir wall, as part of the septum, plug or any structure attached to said opening. The same applies to replace air in the reservoir by a drug-containing solution. A venti-valve is appropriate to fulfill the required performance given the implanted organ or individual will be position adequately to keep the air against said valve.

The reservoir wall protuberance and hollow tube can be incorporated to the external wall during the molding process, by a single molding technique, or by multiple cavities molding. The methods of making said device and hollow tube comprise standard molding techniques, such as injection, compression, transfer and extrusion molding. Alternatively, the hollow tube can be incorporated to the device after the molding process, by a mechanical attachment, and by use of adhesives. An example of the embodiment is a device, wherein said external wall comprises a protuberance having optimally the shape of a tube, funnel or a bevel, to which the hollow tube is engaged or attached during or after the manufacture process. A flexible hollow tube, preferentially made of, but not restricted to a flexible silicone elastomer, comprising a tube with a smaller diameter than the protuberance to be fitted in, is designed to allow a better engagement and stability of the connection and a stable seal of the junction, preventing leakage thereof. Both the refilling port and the hollow tube can be connected to the reservoir by means of junctions and sealed by adhesives.

A long tube can be made connected to the reservoir. Due to anatomical variations of mammalian organisms the tube can have a dead or open end. The appropriate length of the tube should be determined by pre e trans-operative factors. As an example, the superior quadrant of eye harbors an intraocular tumor, e.g. choroidal melanoma. The conjunctiva immediately anterior to quadrant is compromised by a filtering surgery to control the intraocular pressure. The device can still be implanted in the superior quadrant, having its refilling port implanted in the inferior quadrant, where it can accessed without compromising the previous filtering surgery. The superior quadrant of the eye can be assessed by a conventional conjunctival cul-de-sac incision. The temporal sclera is exposed and then, the reservoir is placed in contact with the targeted surface. The lateral rectus muscle is isolated through conventional techniques of strabismus and retinal detachment surgery, the hollow tube connected to the reservoir is passed underneath the muscle, anchored anteriorly in the inferior quadrant, where the refilling port will be situated. The tube can be trimmed down in accordance to the needs of its application during the implantation procedure. In another embodiment, the refilling port comprises a protuberance to allow connection of said hollow tube to the refilling port, wherein said hollow tube has a diameter smaller than the protuberance to allow an engagement of said protuberance, and to prevent leakage from the junction.

Alternatively, the refilling port opening is fitted by a valve, which is composed of two flat dishes to allow adherence and sealing to both the inner side and the outer side of the reservoir wall. Between the dishes there is the hollow plug to fit the opening of the refilling port to allow fluid transport across the valve. The connection between the valve and the proximal end of the tube can be achieved by extending the tube beyond the outer dish of the valve. The parts can be attached by apposition, glue and any methods available to those skilled in the art. Preferentially, elastic materials should be used to allow a better fit of said valve plug into the opening of said refilling port. Silicone rubber, latex can be used. Other flexible and elastic materials are available and can be used. At least one part of the valve can be glued to refilling port. The dishes can be made of elastic and solid materials, and can be incorporated to the valve body during the molding process or afterwards by attachment. Several methods are possible to create said attachment and are known by those skilled with the art.

The diameter of the plug is optimally equal to the diameter of said opening of refilling port, but it can also be slightly larger than the diameter of said opening of the refilling port to allow a better engagement under compression between the valve parts and said refilling port opening, avoiding leakage and dislocation of said valve. The tube is preferentially engaged by the valve, particularly if they are made of different materials. For example, if the valve has a larger diameter than the opening of the refilling port it is ought to be made of an elastic silicone elastomer. After placement of the valve plug into said opening, the elastic material will collapse and the hollow part will obstruct. To avoid this problem, a tube made of a solid silicone elastomer is used and pre-engaged inside the valve. It can be glued or attached by methods available to those familiar with the art.

Preferentially, the inner sides of the dishes are glued to the outer and inner surfaces of the reservoir wall and the plug is glued to said opening of refilling port. Other methods can be used to accomplish seal between the plug and the outer wall. As a non-limiting example the hollow tube can be scrolled into the port. In that case, the thickness of the tube will be preferentially slightly thicker than the receiving port or hole to allow a sealed engagement. Assisted methods for attachment can be used and include photopolymerization, light-induced use of adhesive and heat.

In an embodiment, the refilling port is composed of a self-sealing material, such as a silicone rubber, wherein it has the geometry of a pad, a drum, and any geometry with at least one surface following the curvature of the adjacent tissue, to permit a good accommodation underneath a tissue or a body surface.

The drum may be hollow or composed of the self-sealing material in its full thickness. If more than one device is implanted, one drum can be connected to more than one device, in order to diminish the number of invasive procedures, such as injections, to refill the reservoir(s). Alternatively, the drum may be composed of multiple cavities, distinguishable by means of staining, each connected to at least one hollow tube. Wherein the external membrane of the drum, or perforating septum, is stained by biocompatible dyes, so different cavities connected to different hollow tubes can be distinguished. Alternatively, a hollow tube of multiple cavities can open into different refilling ports, each connected to at least one tube. The refilling ports can be marked or numbered corresponding to the cavity or the function thereof. Said refilling ports can be positioned in accordance to a known sequence, allowing correct identification of the refilling port by its correspondence to the reservoir or agent injected therein. By these means multiple reservoirs can be refilled by different agents keeping the original ascertainment.

Pumps can be connected to the reservoir directly or indirectly by means of tubes and catheters. Pumps are largely available and different technologies can be used depending upon the characteristics of the drug, dose and formulation to be delivered, targeted organ, and locus for implantation of the pump. Pumps can use a variety of technologies to control the injection or delivery rate of compounds from its reservoir. Osmotic pumps are commercially available, the ALZET® and DUROS® pumps (ALZA Corp., Palo Alto, Calif.) and can be used to replenish the reservoir of the delivery system at a constant rate, extending its effective life.

Infusion pumps are available for use to deliver narcotics and pain control chemotherapeutics in a chronic and programmed basis. Their reservoirs can be as large as 10-20 mL (milliliters). The SynchroMed® (Medtronic, Minneapolis, Minn.) is an example of such devices with 10-18 mL reservoirs of the drug solution. It can be replenished and can deliver drugs through a catheter implanted and accessible at a distant site. The catheter, alternatively, once connected to the refilling port of the targeted delivery system, will allow delivery of drugs at a constant rate to the drug reservoir, and from there to the target tissue.

The use of infusion pumps can add advantages over the control of the diffusion rate through the targeted surface. If a good seal is accomplished, which is possible by means of the sealing features provided by this invention, a controlled positive pressure inside the drug reservoir also determines the diffusion rate of the drug through a tissue surface. The use of infusion pumps allows control of the infusion over time. By controlling the infusion rate, if seal exists with the targeted surface, a reservoir composed by all but one impermeable membrane, the pressure inside the reservoir also controlled as well as the diffusion rate through the permeable membrane, which constitutes the targeted tissue interface. The membrane characteristics of organ surfaces were demonstrated and discussed in background section.

MANUFACTURE AND ASSEMBLING: Drug delivery devices can be constructed by preparing stainless steel single or multicavity molds. These molds can be of two types. Either the molds could be designed as (1) two piece mating pairs for use with a injection molding machine that would force molten polymer in to the cavity. The injected polymer would then be cooled so that it would retain the shape of the cavity, the mold would be split, and the molded drug delivery device would be ejected from the cavity. Alternatively, (2) a vacuum-forming mold could be designed for use with sheet stock that would be heated up to a softening point of the polymer. The polymer, in the form of a sheet, would them be sucked down into the mold and allowed to cool. After the polymer was cooled, the sheet with its drug delivery device depressions would be removed from the mold. It would be stamped cut to produce individual drug delivery devices. Other existing molding techniques can be used depending upon the characteristics of the material to be used. Variations of the technique can be anticipated.

To produce said drug delivery device with a refilling port, a small hole can be molded into or subsequently punched or drilled into the finished drug delivery device. The hole will be fitted with a small silicone septum that will allow the physician to reintroduce more drug or agent after the initial dose has been depleted. The septum is easily penetrated via a fine hypodermic needle, yet after it is withdrawn, the drug will not leak out.

To attach the adhesive to the drug delivery device, sheets of hydrogel adhesive would be applied to a release liner. Rims, the size of the flange of the drug delivery device, would be dye cut through the hydrogel adhesive. The outer cut would only partially penetrate into the release liner. The inner cut would completely cut through the release liner. All excess adhesive outside of the rims as well as the inner oval (adhesive and release liner) would then be removed from the release liner adhesive rim assembly. The drug delivery device produced above would then be positioned over the oval space. Each assembly would be pressed over a spherical mandrel to assure that full contact between the hydrogel and the drug delivery device was achieved. At this point it may be advantageous to separate the partially cut release liner from the remainder of the sheet if individual drug filling of the drug delivery device is desired. If mass production techniques are anticipated, retaining the drug delivery devices in an ordered array may be more appropriate.

The drug delivery device can be filled with any form or state of the drug or agent or with any filler or binder in which the drug or agent is stable, and from which, the drug or agent can be readily delivered to the scleral tissue of the eye. It can be accomplished after implantation of the device with an empty reservoir, transoperatively and in the postoperative period. It can also be accomplished by filling and loading the drug into reservoir before the device is implanted, during the manufacture process and during surgery but before its application to the targeted tissue. If the storage form or state is solid after being poured into the drug delivery device as a fluid, the contents will be self contained. A binder such as those made of Intelimer® (Landec Corporation, Menlo Park, Calif.) materials, chosen from materials that exhibits a solid to liquid transition at determined temperature, as non-limiting example of about 35° C., or slightly below the body temperature could be used to stabilize the storage form but would transform into a fluid form after exposure to the warmth of scleral tissue upon application. If the storage state is fluid, there is a need to contain the liquid by an addition membrane for structural purpose. In addition, upon removal, the application of a cooling probe could solidify the solution and facilitate its removal. The thin membrane could be one made of a Intelimer® (Landec Corp., Palo Alto, Calif.) polymer which would not be sensitive to an aqueous vehicle but would rapidly deteriorate when exposed to the 35-37° C. temperature of the eye. Alternatively, a biodegradable polymeric membrane such as a copolygylcolic-lactic acid material could be used, provided that the liquefying vehicle was not aqueous based. In this case the moisture from the scleral tissue would cause the integrity of the membrane to deteriorate and allow the passage of the drug containing in the reservoir.

THERAPEUTIC AGENTS: Any diagnostic and therapeutic compounds can be carried in the delivery system. An example of diagnostic applications of such system is the monitoring of the trans-liver capsule diffusion after liver surgery. Having the device being implanted onto the liver surface, it can deliver a therapeutic compound in association or not to a diagnostic agent. Gadolinium is a non-toxic agent that is largely used in radiology for imaging of living tissues. This is commercially available for clinical use and is sensitive to nuclear resonance imaging techniques. Gadolinium can be injected and loaded into the device in association or not to the therapeutic compound after, during or before the implantation procedure. The diffusion of the diagnostic agent through its capsule can be useful in monitoring the diffusion surface for therapeutic agents similarly delivered by the device. In addition, the delivery of a diagnostic agent can also have pure diagnostic purposes, as for monitoring the recurrence or growth of a surgically excised tumor in the postoperative period. Other diagnostic agents can be used, including radiosensitive diagnostic compounds for use with computerized tomography and/or x-ray. These agents are largely available for clinical application and its use is widespread.

Example of drugs with potential for being delivered from the medical device can be chosen from the class of sulfonamides, e.g. acetazolamide; steroidal anti-inflammatory agents, e.g. triamcinolone, dexamethasone; non-steroidal anti-inflammatory agents, e.g. ketorolac, piroxicam, tenoxicam, indomethacin; alkaloids; prostaglandin and derivatives, antibiotics, antivirals and immune-modulators.

Verterpofin (Visudyne™, Novartis AG, Basel, Switzerland) is a photosensitizer. It is usually injected intravenously in order to achieve high levels in vascularized tissues. The spot size of the laser will determine its effect. Alternatively, if verterpofin is delivered by the targeted delivery system, a greater diffusion of the agent can be accomplished even in non-vascularized tissues, leading to higher effect of the stimulating laser. A potential application for this use is in intraocular tumors and conditions that lead to the development of subretinal membranes, such as age-related macular degeneration. Having not only the vessels being occluded in these pathologic tissues, but also the interstitial part of the tissue, a lower rate of regrowth of the tissue may be the result. PKC412 (Novartis AG, Basel, Switzerland) is an agent demonstrated to interfere with the process of neovascularization by inhibiting the protein kinase C. PKC 412 is a non-limiting example of the applicability of the present invention. It has efficacy demonstrated being delivered by the periocular route by simple injections and being administered orally. As for the periocular route ocular irritation and toxicity was observed, when administered side effects such as nausea and diarrhea were found. PKC412 is efficacious but its effectiveness is limited by its toxicity, particularly in the case of eye diseases. PCK412 is suitable for delivery from the present invention and can be associated to a variety of compounds to retard or control its release.

Other compounds have demonstrated great potential for treatment of ocular conditions, particularly intraocular tumors. As it was demonstrated, transducible peptides are efficacious against ocular melanoma and retinoblastoma. (16) Their efficacy, however, can only be translated to effectiveness if the delivery route is feasible. Intravitreal injections do not permit drug delivery into eyes with intraocular tumors due to the risk of systemic dissemination of the tumor cells. In that scenario, the eye barriers have to preserved and the drugs still effectively delivered into the tumor-harboring eye. Transducible peptides are agents with high potential of effectiveness if delivered by this system. Agents that lend themselves characteristics of diffusion-capable and beneficiaries of this art include molecules selected from the class of anti-vitral, antibiotic, cytoxic, opioid, peptide, nucleotide, enzyme, COX-inhibitors, steroid, morphine, beta-blocker, alfa-agonist, prostaglandin, sulfonamide, chelant, antibody, nano-molecules, immunosupressants such as cyclosporin; magnetic, radio and immuno labeled-agents; anti-cancer agents such as 5-fluorouracil, carboplatin, cisplatin, etoposide, topotecam, vincristine, adriamycin, nitrogen mustard, ifosfamide, cyclosfosfamide and related compounds; antiglaucoma drugs such as beta-blockers: timolol, betaxolol and atenalol, prostaglandin analogues, alfa-agonists; carbonic anhidrase inhibitors such as acetazolamide and dorzolamide constitute non-limiting examples of agents potentially delivered by the present invention.

Several cytotoxic agents have been shown to be efficacious against tumor cell lines. Unfortunately, when combining therapeutic agents to accomplish a maximum therapeutic effect, one has to limit the possible combination by the side and toxic of effects of multiple drugs and potential exacerbation of toxicity due to drug interactions. The ideal combination does not need to be delivered all by the same route. To minimize systemic toxicity due to systemic drug interaction, another route can be used to administer the second drug. Wherein two or more therapeutic agents are used in combination, the first therapeutic agent is administered by a route such as intravenous and a second therapeutic agents is delivered by the present invention. Numerous combinations are possible of routes and therapeutic agents. The present invention can be associated with the use of topical, subconjunctival, subTenon, retrobulbar, intravitreal, peribulbar, intravenous, intramuscular, subcutaneous and intracameral. The first therapeutic agent can be a pro-drug and second the complementary agent to start the therapeutic effect, and vice-versa. At least one agent can be the therapeutic sensitizer and the second, the initiator of the therapeutic effect. For example, if the first is a light-sensitive dye delivered by the present invention, the second will be the stimulating-light at the wavelength requirement of the first agent. Several combinations are possible. A pro-drug can be delivered by the present invention while the second agent will be injected intravitreally to provide activation of the pro-drug in situ.

As other non-limiting examples of other therapeutic agents that could be carried and delivered using the present invention include the classes of anesthetics and pain killing agents such as lidocaine and related compounds, anti-fungal agents such as fluconazole and related compounds; anti-viral agents such as trisodium phosphomonoformate, trifluorothymidine, acyclovir, ganciclovir, DDI and AZT; cell transport/mobility impending agents such as colchicine, vincristine, cytochalasin B and related compounds; antihypertensives; decongestants such as phenylephrine, naphazoline, and tetrahydrazoline; immunological response modifiers such as cyclosporin, muramyl dipeptide and related compounds; peptides and proteins such as insulin, growth hormones, insulin related growth factor, heat shock proteins and related compounds; steroidal compounds such as dexamethasone, prednisolone and related compounds; low solubility steroids such as fluocinolone acetonide and related compounds; carbonic anhydrase inhibitors; diagnostic agents; antiapoptosis agents; gene therapy agents; sequestering agents; reductants such as glutathione;

antipermeability agents; antisense compounds; antiproliferative agents; antibody conjugates; bloodflow enhancers; antiparasiticagents; non-steroidal anti inflammatory agents such as ibuprofen, indomethacin; nutrients and vitamins: enzyme inhibitors: antioxidants; anticataract drugs; aldose reductase inhibitors; cytoprotectants; cytokines, cytokine inhibitors, and cytokin protectants; mast cell stabilizers; and anti neovascular agents such as pigment epithelium derived growth factor (PEDF), PEDF-expressing gene vectors such as adenovirus-PEDF, inhibitors of vascular endothelial growth factor and fibroblast growth factor, matrix metalloproteinase inhibitors and derivatives thereof.

Examples of agents also include neuroprotectants such as nimodipine and related compounds; antibiotics such as tetracycline, chlortetracycline, bacitracin, neomycin, polymyxin, gramicidin, oxytetracycline, chloramphenicol, gentamycin, and erythromycin; sulfonamides, sulfacetamide, sulfamethizole, sulfisoxazole; nitrofurazone, and sodium propionate; antiallergenics such histamine receptor blockers; anti-inflammatories such as hydrocortisone, hydrocortisone acetate, dexamethasone 21-phosphate, fluocinolone, medrysone, methyiprednisolone, prednisolone 21-phosphate, prednisolone acetate, fluoromethalone, betamethasone and triminolone; miotics and anticholinesterase such as pilocarpine, eserine salicylate, carbachol, di-isopropyl fluorophosphate, phospholine iodine, and demecarium bromide; mydriatics such as atropine sulfate, cyclopentolate, homatropine, scopolamine, tropicamide, eucatropine, and hydroxyamphetamine; svmpathomimetics such as epinephrine; and prodrugs thereof.

ADHESIVES: Acrylates and its derivatives are also available for clinical use and demonstrate a high binding strength. Ricci and Ricci demonstrated good compatibility of buckling implants in apposition to the sclera using a cyanoacrylate derivative.(12) Cyanoacrylate has been approved for human use as tissue adhesive, n-Butyl-2-Cyanoacrylate monomer, (Indermil™ Tissue Adhesive, Tyco Healthcare Group, LP, Norwalk, Conn.). The biocompatibility and safety of derivatives of cyanoacrylate allowed its approval also for causing embolization of malformed blood vessels after its injection through a hollow tube, n-Butyl Cyanoacrylate (TRUFILL®, Cordis Neurovascular, Inc., Miami Lakes, Fla.). The adhesive layer can be applied just before the implantation procedure or pre-applied by means of transferring and use of release liners and films.

Pressure sensitive adhesives (PSA) can be built on the internal surface of the sealing base. Different types of PSA are commercially available, including acrylates and acrylate-derivatives.

As non-limiting example, the adhesive layer preferentially transferred to the sealing base of the device in the form of transfer adhesives. Transfer adhesives can be manufactured as an adhesive layer between two layers of release liners. Release liners are commercially available and allow the exposure of the adhesive layer after being easily peeled off. After removal of one release liner, the adhesive layer with a release liner on the other side will be exposed. The adhesive is applied to the device surface and the release liner is left in contact with the adhesive layer until the implantation procedure is performed. Before the implantation procedure, the second release liner is removed exposing the adhesive layer overlying the device and sealing base.

Alternatively, a film coated with adhesive in both sides can be used. An adhesive layer on the outer surface of the film, or first adhesive, will adhere said film to the device surface, letting the other surface of the film, also containing an adhesive layer, or second adhesive, exposed to be later applied to the targeted tissue or organ. Said first adhesive is chosen to based on the device and sealing base material. The second adhesive is chosen based on the targeted surface and organ where the device in going to be applied.

Combinations of adhesives are possible depending upon the material of the device and targeted surface. Silicone, acrylic and rubber based adhesives are preferentially used in combination or not. As non-limiting example, 3M Medical Specialties (3M Corporation, St. Louis, Minn., USA) make commercially available a series of transfer, or unsupported, single coated and double coated adhesives. As for double coated adhesives, an inner layer of an acrylic-based adhesive can be used with an outer layer of rubber-based adhesive. A film can separate both and be made of different materials by those skilled in the art. Combination of different PSAs is also desirable depending upon the size and surface of the targeted tissue, characteristics of the drug and design of the device, and implantation procedures. Release liners can be present in contact with the adhesive and to be peeled off before the implantation procedure, exposing the adhesive layer.

Commercially available adhesives include acrylic, rubber and hydrocolloid based, which are built to surfaces and involving also release liner. Several brands are available, such as Velcro® (Velcro Inc., Manchester, N.H.) and ARCare® (Adhesives Research Inc., Glenrock, Pa.). Silicone pressure-sensitive adhesives are also commercially available, such as from Dow Corning® brand (Dow Corning Corp., Midland, Mich.). Release liners are widely available and can be designed according to the adhesive layer by the ones skilled in the art. Absorbent hydrocolloids constitute another category adhesives that fit the requirements for adhering to mucosal surfaces. Hydrocolloid adhesives are commercially available for example by Avery medical adhesives (Pasadena, Calif.) and 3M Medical Specialties (3M Corporation, St. Louis, Minn., USA).

Compositions that permit the sealing base to be implanted and adhered to the bared surface of the targeted tissue, interpositioned or not by a film can be used herein. This art is aimed to permit implantable devices to be sealed attached to surgically exposed surfaces of organs or tissues.

Adhesives and polymers with adhesive properties can be activated during the implantation procedure by acceleration of the polymerization. Photopolymerization is a well-known initiator and accelerator of the polymerization process and can be used in vivo, during the implantation procedure by light-emitting devices. Chemical alternatives are available and can initiate the polymerization process. Said adhesives, polymers and methods for polymerization can be manufactured, designed, incorporated and applied by those skilled with the art. Polymers for dental application constitute and examples of high-bond attachments created in vivo by methods of photo and chemical polymerization.

FILMS AND MEMBRANES: Films with different compositions and at different ratios can be used to delineate the reservoir. Besides providing a structural support for the formulation contained in the reservoir, it can also control the permeation of the reservoir by water influx for the target surface as well as the permeation of the target surface by the drug.

The impermeable surface of the device can be coated by cellulose and its derivatives. Ethylcellulose is commercially available and can be used to manufacture an impermeable external surface for the reservoir (ETHOCEL®, Nissin Kasei Co. Ltd., Osaka, Japan). Other materials are also commercially available, as non-limiting examples are the different backing materials such as polyurethane by 3M Drug Delivery (3M Corporation, St. Louis, Minn., USA).

Cellulose can be used to make the drug-containing tablets to be fitted into the drug reservoir. Cellulose and derivatives are commercially available (Avicel®, Asahi Kasei Co., Ltd., Osaka, Japan).

Membranes of ethylene-vinyl-acetate (EVA) are largely available. The permeability to molecules is well know for EVA membranes and shown to increase as the concentration of EVA increases in the membrane. Preferentially, membranes with concentration ranging from 1% to 30% are used, but any concentration can be desired depending on the application of the device, drug, membrane characteristics of the targeted surface, formulation are among the factors that dictate the concentration of EVA and permeation rate of the membrane to be used. EVA membranes are commercially available for that purpose. As non-limiting examples are the membranes produced by 3M Drug Delivery (3M Corporation, St. Paul, Minn., USA).

Other technologies are widely available and applied to carry and encapsulate drugs, protecting it from the surrounding fluids and tissues and vice-versa, particularly before they reach the absorptive mucosa of the intestinal tract and other hostile environments. Encapsulation has long been used and available to carry drugs and its formulations. Several compounds, blends and methods can be used. Herein, the same art can be applied to protect premature exposure of the agents to the internal body tissues and fluids, and vice-versa.

If the structural and functional characteristics of the device, its contents and application require the use of non-biocompatible materials, another coating layer can be introduced to improve such biocompatibility. As a non-limiting example, silicone elastomer is a material largely used for encapsulating medical devices such as pacemakers, delivery pumps and electronic chips before they are implanted into body tissues. Other arts are available and can be applied herein.

MANUFACTURING AND ASSEMBLING DRUGS INTO RESERVOIR

Tablets can be made by a variety of techniques, e.g. manual compression. The molds are designed to meet the reservoir dimensions. Alternatively they can be suspended in the reservoir as a viscous or liquid solution that will further provide stability of such compositions in said reservoir. Micro or macro-encapsulated agents are carried suspended or freely in the reservoir. Additional methods can be used to provide stability to such agents in the reservoir and are discussed below.

Compressed tablets can be held in place in the reservoir by a structural membrane, preferentially composed of a rapidly degradable polymer, covering the release port of the reservoir. Several compositions are available. Films of lactide, glicolide and cellulose are non-limiting examples. Other arts are available and largely available by and for the pharmaceutical industry and by the skilled in the art.

Alternatively, a series of strips and/or bands, herein tablet structural holders, can be built extending beyond the opening of the release port, wherein said strips are preferentially composed of the same material used to make the sealing base. Said strips and bands, preferentially, follow the targeted surface or tissue curvature, but if built of elastic materials, such as a silicone elastomer, it can across the opening through its diameter without respecting the curvature of said targeted tissue. Several variants of shapes, thickness, width and length of the bands and strips can be built depending upon the characteristics of the tablet to be contained in the reservoir and the material to be used. Ideally, the width of the strips or bands should be one to do not interfere with the diffusion interface between the release port and the targeted surface. The total area of the bands and strips in the release port should be taken into account in calculating the diffusion area with the targeted surface. Alternatively, if solid materials are used, the strips and be built at a level of the reservoir where it does not interfere with the attachment between the device and the targeted tissue.

Said strips and bands can be molded and made as part of a sealing base platform and can incorporated to the sealing base and device after its molding and manufacture. For example, if the sealing base is made separately from the reservoir, said bands and strips can be built as part of the sealing base molding and to be attached to the reservoir along with the sealing base, containing said compressed drug formulation or tablet. Alternatively, said bands and strips can be incorporated to the sealing base and device by means of attachment. Adhesives are preferentially used to attach said bands and strips to sealing base and device. Silicone elastomers and hydrogels are example of materials largely available for this purpose and used by ones skilled in the art. In another embodiment, the strips, bands and flanges built to hold the tablet in the reservoir are made of an elastic material such as an elastic silicone elastomer or rubber, latex, rubber derivatives. The methods of incorporation of said tablet, solid or viscous composition to said reservoir in the presence of said tablet holders include but are not limited to mechanical apposition, attachment assisted by adhesive and compression.

An embodiment of the present invention comprises a flat platform, which is attached to said sealing base or to said reservoir wall, and present at least one fenestration. Said fenestration represents a window for diffusion of said agents contained in such reservoir to the target organ or surface. Said platform represent a structural retainer of the continents of said reservoir and a functional part of said device by determining the window area through which the diffusion will take place. Said platform is preferentially placed in apposition to the target surface. In such circumstance the platform window will represent the ultimate diffusion interface area. In another embodiment, the platform is placed in just apposition or no direct apposition to the surface. In such circumstance, a fluid meniscus between said platform and target surface will extend beyond the interface area, but still limited to the area sealed and delineated by the sealing base. The contact area between said fluid meniscus and target surface or organ represents the ultimate organ-drug interface.

Another embodiment of said platform comprises several fenestrations. If said platform if maintained in apposition to said target surface the sum of the of areas of said fenestrations will represent the final interface area where the drug exchange occurs. Alternatively, if said platform is steep in relation to the sealing base-defined surface, said platform will be not in apposition to the target surface and the fluid meniscus between said platform and said target surface will determine the interface and exchange area.

The diameter of said fenestration and the number of fenestration and the relation between diameter and number of fenestrations in the above embodiments are dependent on several factors, including but not limited to the viscosity of the compound carried in the reservoir, dose, stability, target surface and organ, active agent, formulation of said active agent, whether for slow and controlled release or not, and method of application.

In another embodiment, said platform is composed of compounds chosen preferentially from the class of silicone, hydrogel, poly-ethylene, poly-orthoester, poly-glycolic acid, poly-lactic acid, poly-caprolactone, polyvinyl-alcohol, polyvinyl-pyrrolidone and metals. Said platform may comprise and incorporate a membrane to fill said fenestration. Wherein said membrane has the same composition of said dissolvable films. Wherein said membrane has the same composition of said platform. Wherein said membrane has said tablet holder structures and accessories and said membrane comprises further fenestrations or at least one fenestration.

The incorporation of said platform to the reservoir wall is done by mechanical, chemical attachment or gluing and physical attachment. Such incorporation is preferentially done before its application, but can be performed during the implantation procedure. In addition, it can be complemented or not by physical or chemical methods of polymerization.

Alternatively a barrier membrane can compose said release port and hold the active agent and formulation in place. It can also control the release rate of the active ingredient. Several polymer attain the characteristics necessary to provide mechanical stability to the active ingredient while controlling the release of the active ingredient from the reservoir. Ethylene-vinyl acetate (EVA) at different concentrations accomplishes both characteristics. A film or membrane of said EVA can be built covering the release port. The thickness of said film ranges between 1 um (micrometers) to 800 um. Ideally, it varies from 50 um (micrometers) to 200 um. The content of EVA in the film is to be determined upon the characteristics desired for the drug release pattern, drug and targeted tissue. It can range from 0.5 to 99%, but optimally ranges from 2 to 30%. The film can be interpositioned between the different parts of the device and can also be attached to said device by means of adhesives. The external surface of said membrane can contain an additional layer of adhesive which will adhere to the target surface. The membrane area covers at least one release port from one reservoir and can extend beyond the limits of said release port to cover the internal surface of the sealing base. A release liner can be further incorporated to the external surface of the membrane, which will be in contact with the target surface. Said release liner will be peeled off before the implantation procedure, exposing the adhesive-covered surface of the membrane.

Other methods can be applied as well as other membranes known by those skilled in the art. Several compounds are available for composition of such barrier membranes as well as adhesives for biological use. In an alternative embodiment, a biodegradable membrane is used. If a biodegradable composition is applied, the membrane will be dissolved after implantation procedure. Nevertheless, it constitutes a barrier avoiding premature exposure of the reservoir ingredients to external and internal-to-the-body factors.

Alternatively, the adhesive can contain the drug itself and both reservoir and biodhesive layer contain the active agent. The external wall is still required to minimize the diffusion of agents outwards its external surface and to provide mechanical stability to the device. A backing layer or film can be applied to the composition and provide the required no diffusion or minimum diffusion requirements to exert its role. As non-limiting example, polyurethane backing films are available and can be applied to said device wall by means of heat or adhesive-assisted attachment.

The drug reservoir whether encapsulated or not, can be applied to the reservoir by means of methods largely available and used by the pharmaceutical industry. It includes but is not restricted to glue, polymers, adhesives, photopolymerization, compression, mechanical attachment, anchoring. Solid drug consisting of pellets, capsules, packed compounds and compressed solids can be attached to the reservoir by use of glue, mechanical engagement and attachment. This is largely available and several techniques are available. As an example of encapsulated agents, the U.S. Pat. No. 6,258,870 discloses methods for encapsulating biological agents. Several other methods are available and can be used in the present invention.

MATERIALS: Naturally occurring or synthetic materials that are biologically compatible with body fluids and eye tissues and essentially insoluble in body fluids which the material will come in contact include, but are not limited to, glass, metal, ceramics, polyvinyl acetate, cross-linked polyvinyl alcohol, cross-linked polyvinyl butyrate, ethylene, ethylacrylate copolymer, polyethyl hexylacrylate, polyvinyl chloride, polyvinyl acetals, plasticized ethylene vinylacetate copolymer, polyvinyl alcohol, polyvinyl acetate, ethylene vinylchloride copolymer, polyvinyl esters, polyvinylbutyrate, polyvinylformal, polyamides, polymethylmethacrylate, polybutylmethacrylate, plasticized polyvinyl chloride, plasticized nylon, plasticized soft nylon, plasticized polyethylene terephthalate, natural rubber, polyisoprene, polyisobutylene, polybutadiene, polyethylene, polytetrafluoroethylene, polyvinylidene chloride, polyacrylonitrile, cross-linked polyvinylpyrrolidone, polytrifluorochloroethylene, chlorinated polyethylene, poly(1,4'-isopropylidene diphenylene carbonate), vinylidene chloride, acrylonitrile copolymer, vinyl chloride-diethyl fumerale copolymer, butadiene/styrene copolymers, silicone rubbers, especially the medical grade polydimethylsiloxanes, ethylene-propylene rubber, silicone-carbonate copolymers, vinylidene chloride-vinyl chloride copolymer, vinyl chloride-acrylonitrile copolymer and vinylidene chloride-acrylonitride copolymer.

Biocompatible compounds can be used in parts of the device include cross-linked alginates, gelatin, collagen, cross-linked collagen, collagen derivatives, such as, succinylated collagen or methylated collagen, cross-linked hyaluronic acid, chitosan, chitosan derivatives, such as, methylpyrrolidone-chitosan, cellulose and cellulose derivatives such as cellulose acetate or carboxymethyl cellulose, dextran derivatives such carboxymethyl dextran, starch and derivatives of starch such as hydroxyethyl starch, other glycosaminoglycans and their derivatives, other polyanionic polysaccharides or their derivatives, polylactic acid (PLA), polyglycolic acid (PGA), a copolymer of a polylactic acid and a polyglycolic acid (PLGA), lactides, glycolides, and other polyesters, polyoxanones and polyoxalates, copolymer of poly(bis(p-carboxyphenoxy)propane)anhydride (PCPP) and sebacic acid, poly (1-glutamic acid), poly(d-glutamic acid), polyacrylic acid, poly(dl-glutamic acid), poly(1-aspartic acid), poly(d-aspartic acid), poly(dl-aspartic acid), polyethylene glycol, copolymers of the above listed polyamino acids with polyethylene glycol, polypeptides, such as, collagen-like, silk-like, and silk-elastin-like proteins, polycaprolactone, poly(alkylene succinates), poly(hydroxy butyrate) (PHB), poly(butylene diglycolate), nylon-2/nylon-6-copolyamides, polydihydropyrans, polyphosphazenes, poly(ortho ester), poly(cyano acrylates), polyvinylpyrrolidone, polyvinylalcohol, poly casein, keratin, myosin, and fibrin. As non-limiting examples they can constitute at least a part of said device. Multiple agents with different characteristics can be used in the same device.

The device of the present invention can be built using biodegradable and non-biodegradable polymers. To minimize the diffusion of agent outwards the drug reservoir to the surrounding tissues while allowing diffusion to the target organ or tissue, a single or a combination of polymers can be used. Several embodiments can be used and are exemplified therefore.

As a non-limiting example of biodegradable device, polyglycolic (PGA) and poly-lactic (PLA) acid can be used at different proportions. An external wall can be predominantly or solely made of PGA to allow a prolonged and slower dissolution rate. A 100% PGA composition will minimize the diffusion of agents from the reservoir outwards the reservoir and will provide prolonged structural stability to the implant. Lower proportions of PGA are possible depending on the length of effect and drug release the device is aimed to attain. For shorter periods more rapid degradation of the device may be desired and if so, a lower concentration of PGA is used. For example, PGA/PLA 7:3 can be used and several other concentrations can be applied depending upon other characteristics of the drugs and of the other parts of the implant. More importantly, the release port membrane has to attain a more rapid degradation than the external wall. In the example of the 100% PGA, a 80:20 PGA/PLA composition can allow degradation of release port membrane over a short period of time in order to start the diffusion of agent thought the target organ surface. Other proportions of compositions are predicted based on characteristics of drugs, disease, organ, design, pharmacokinetics and pharmacodynamics of agents to be used and formulations thereof. Biodegradable membranes are commercially available and can be designed by third parties in order to fulfill specific design requirements of the present inventions by those skilled in the art.

In order to provide a better stability of the carried therapeutic agents, biocompatibility of the system and/or its parts, control of inflammation, improve of application and/or feasibility of clinical use, coating agents can be required. Such agents can be functional in controlling the release of the agents, dissolution of membranes or polymers, or by controlling the reaction of the body to the system, as by controlling inflammation and fibrosis. Several arts were developed and are widely known by those skilled in the art, particularly in the pharmaceutical industry. As that art, several arts are described and available to be used in the construction of the present invention.

NON-LIMITING EXAMPLES OF ADVANTAGEOUS USE OF THE PRESENT INVENTION

The delivery system described in this application differs in concept from all of the local delivery systems described above. This system addresses several of their design and functional limitations, and incorporates advances achieved in polymer and slow-release technology.

Insertion of the medical device is done either with minor local surgery as in the case of the eye or with minimally invasive surgery, e.g., endoscopic procedures, for deeper organs. Sealed attachment to the surface of the target organ is crucial for the system to function properly. A watertight seal can be achieved by means of a suture, but ideally would employ pre-applied bioadhesives.

The tissue-targeted delivery system has potential broad applicability to the treatment of any pathologic process that is localized.

Examples of organ-confined malignancy and a destructive neovascularization process are presented below. Other local processes to which the present invention could be applied include infection, and inflammation among others. For the sake of brevity these are not discussed further. Two pathologic processes of the eye are mainly The treatment of most diseases today requires a careful balance between the therapeutic efficacy of any specific agent and the unwanted side effects to be expected from its use. The intervals between cycles of chemotherapeutic agents for malignant disease are necessary to allow the body to recover from unwanted systemic toxicity. This cycling of treatment may not be the most efficacious way to deliver therapy to the disease but it cannot be avoided. The development of bio-targeted agents promises some relief from the side effects of today's drugs on normal tissue. However, the costs associated with new agent development are enormous and their long-term side effects are not well understood. Targeted delivery systems are relatively economical, and hold the possibility of extending the life span of drugs already on the market.

The delivery system described in this application differs in concept from all of the local delivery systems described in the Background section. The reservoirs of the present invention can be pre-filled, pre-sterilized and sealed. The chambers can be applied in any number, configuration or combination needed. It is possible to simultaneously apply many different agents, each of which may work in a different way to achieve better disease response. In addition to the possibility of multiple device implantations, multimodality therapy may also be achieved by mixing compatible agents in the same delivery reservoir. All of this can be accomplished while virtually eliminating local or systemic side effects.

Insertion of the present invention is done either with minor local surgery as in the case of the eye or with minimally invasive surgery, e.g., endoscopic procedures, for deeper organs. Hermetic attachment to the surface of the target organ is crucial for the system to function properly. A watertight seal can be achieved by means of a suture, but ideally would employ pre-applied bioadhesives. Impermeable yet malleable material can allow the sealing base of the reservoir to adapt to the shape of irregular tissue surfaces.

The present invention has potential broad applicability to the treatment of any pathologic process that is localized or systemic but initiated or regulated by the targeted tissue. Examples of organ-confined malignancy, neovascularization of retina, choroidal neovascularization, glaucoma, uveitis, endophthalmitis, vitritis, proliferative vitreo-retinopathy.

Retinoblastoma is chosen as an example of organ-confined malignancy, not because it is common, but because it shares features with many organ-confined diseases that are difficult to treat safely with non-targeted systemic therapy. In addition, it is confined to the organ or origin until very late in the course of the disease.

Current Therapy: The current treatment for moderately advanced intraocular retinoblastoma involves systemic administration of cytotoxic agents followed by local consolidation with transpupillary laser or transscleral cryotherapy. The usual regimen is 6 cycles of systemic chemotherapy consisting of carboplatin, etoposide, and vincristine with local consolidation following each cycle if necessary. The cost of the treatment course with all of the associated required testing, local laser consolidation and surveillance under general anesthesia until age 3 years can amount to more than $200,000. Combined modality therapy, consisting of adding bioactive anti-tumor peptides and anti-angiogenesis proteins, would be prohibitively expensive if given systemically.

In addition to the cost of treatment, the systemic toxicity of this chemotherapy is significant, especially so in infants and small children. Bone marrow suppression with an increased risk for septicemia and the need for blood transfusions is expected. The side effects are so significant that in the case of advanced unilateral retinoblastoma, when the fellow eye is normal, systemic chemotherapy is rarely recommended, and surgical removal of the eye (enucleation) is considered to be better for the child.

Protection Against Local Orbital or Periocular Toxicity: The periocular delivery of therapeutic agents is employed when increased amounts of the agent are needed inside the eye. In the case of advanced intraocular retinoblastoma, tumor cells in the vitreous gel are not exposed to sufficient amounts of the chemotherapeutic agents. For this reason, local periocular carboplatin is added to the regimen of systemic chemotherapy for advanced disease. The periocular injection or irrigation of carboplatin is well tolerated by the local tissue when a bolus is injected into the periocular space. However, in a Phase I study of the toxicity of local carboplatin we saw long-term toxic effects consisting of atrophy of the orbital fat and connective tissue following 6 local injections of carboplatin. Etoposide, another agent effective against retinoblastoma is extremely toxic when administered locally and has not been able to be used for local augmentation. Mulvihill et al. reported the complications associated with periocular injections of the chemotherapeutic agent carboplatin in infants with retinoblastoma. This emphasizes the need of a sealed system for unidirectional delivery of toxic agents to the eye.

The Potential of Delivering Multi-modality Therapy: The use of implantable agent delivery reservoirs opens the possibility that combinations of agents may be administered simultaneously. As an example, there are many pathways available to therapeutically interfere with the growth and survival of intraocular retinoblastoma. We have generally relied only one pathway in the clinical treatment of this disease. By attacking multiple pathways of tumor growth simultaneously, significant progress has been achieved in the treatment of another cancer, metastatic melanoma. In that disease concurrent treatment consisted of a combination of cytotoxic agents, interleukin, and interferon. Similar potential advances could come with the simultaneous use of multiple chambers all attached to the same organ but delivering different therapeutic agents.

Choroidal neovascularization (CNV) due to age-related macular degeneration is the most common cause of severe vision loss in Americans over the age of 60. Most of the available treatments aim to prevent further vision loss instead of restoring visual function. Laser photocoagulation can be used to ablate CNV, but recurrences are common. Photodynamic therapy can shut down CNV but still damage to overlying retina will exist. Recurrences are common and are attributed to the lack of therapeutic agents to control the underlying angiogenic stimuli. Several agents, including VEGF antagonists such as monoclonal antibodies, monomers of said antibodies, antisense nucleotides, peptides and steroids may suppress CNV growth and leakage. The administration of such agents, however, requires repeated intravitreal injections, which are associated with complication due to disruption of the ocular integrity. The method of drug delivery of the present invention can offer advantages over current methods and can enable several therapeutic agents to be used clinically by overcoming the drawbacks of the prior art.

USPTO REFERENCES

U.S. Pat. Nos. 6,217,895; 6,001,386; 5,902,598; and 5,836,935, to Ashton et al., and U.S. Pat. Nos. 6,416,777 and 6,413,540, to Yaacobi et al.

BACKGROUND SECTION REFERENCES

1. Mulvihill A, Budning A, Jay V, Vandenhoven C, Heon E, Gallie B L, et al. Ocular motility changes after subtenon carboplatin chemotherapy for retinoblastoma. Arch Ophthalmol 2003; 121(8):1120-4.
2. D'Hermies F, Korobelnik J F, Meyer A, Morel X, Behar-Cohen F, Bertin S, et al. [Histological changes related to scleral buckling for treatment of retinal detachment]. Clin Exp Pathol 1999; 47(5):215-22.
3. Korobelnik J F, D'Hermies F, Ducourneau D, Legeais J M, Chauvaud D, Hoang-Xuan T, et al. e-PTFE as scleral buckling episcleral implants: an experimental and histopathologic study. J Biomed Mater Res 1999; 48(6):807-13.
4. D'Hermies F, Korobelnik J F, Chauvaud D, Pouliquen Y, Parel J M, Renard G. Scleral and episcleral histological changes related to encircling explants in 20 eyes. Acta Ophthalmol Scand 1999; 77(3):279-85.
5. D'Hermies F, Korobelnik J F, Meyer A, Chauvaud D, Pouliquen Y, Renard G. Experimental encircling scleral buckle with silicone and hydrogel: histopathologic and comparative study of 26 rabbit eyes. Retina 1999; 19(2): 148-57.
6. D'Hermies F, Korobelnik J F, Caputo G, Mashhour B, Chauvaud D, Pouliquen Y, et al. Encapsulation of scleral buckling materials. A study of sixty specimens. Ophthalmology 1998; 105(6):1079-86.
7. D'Hermies F, Korobelnik J F, Savoldelli M, Chauvaud D, Pouliquen Y. Miragel versus silastic used as episcleral implants in rabbits. An experimental and histopathologic comparative study. Retina 1995; 15(1):62-7.
8. Korobelnik J F, D'Hermies F, Chauvaud D, Legeais J M, Hoang-Xuan T, Renard G. Expanded polytetrafluoroethylene episcleral implants used as encircling scleral buckling, an experimental and histopathological study. Ophthalmic Res 2000; 32(2-3):110-7.
9. Spitznas M, Lossagk H, Vogel M, Meyer-Schwickerath G. Retinal surgery using cyanoacrylate as a routine procedure. Albrecht Von Graefes Arch Klin Exp Ophthalmol 1973; 187(2):89-101.
10. Calabria G A, Pruett R C, Refojo M F, Schepens C L. Sutureless scleral buckling. An experimental technique. Arch Ophthalmol 1970; 83(5):613-8.
11. Calabria G A, Pruett R C, Refojo M F. Further experience with sutureless scleral buckling materials. II. Cyanoacrylate tissue adhesive. Arch Ophthalmol 1971; 86(1):82-7.
12. Ricci B, Ricci F. Octyl 2-cyanoacrylate tissue adhesive in experimental scleral buckling. Acta Ophthalmol Scand 2001; 79(5):506-8.
13. Olsen T W, Y. Yaacobi, M. Parks, R. Flowers, X. Feng, W. Hubbard, et al. An Evaluation of an Episcleral Anecortave Acetate Transscleral Drug Delivery System in Rhesus Monkey. IOVS 2003.
14. Y. Yaacobi, J. Chastain, L. Lowseth, R. Bhatia, E. Slovin, R. Rodstrom, et al. In-Vivo Studies with Trans-Scleral Anecortave Acetate Delivery Device Designed to Treat Choroidal Neovascularization in AMD. In: ARVO; 2003; Ft. Lauderdale: IOVS; 2003.
15. Olsen T W, Aaberg S Y, Geroski D H, Edelhauser H F. Human sclera: thickness and surface area. Am J Ophthalmol 1998; 125(2):237-41.
16. Harbour J W, Worley L, Ma D, Cohen M. Transducible peptide therapy for uveal melanoma and retinoblastoma. Arch Ophthalmol 2002; 120(10):1341-6.

The invention claimed is:

1. An implantable delivery device for delivery of at least a first therapeutic agent into a target tissue, comprising: a housing, said housing comprising a reservoir with a drug release port for release of at least a first therapeutic agent into a target tissue, said reservoir having at least a first wall that is substantially impermeable to a first therapeutic agent to be placed therein, a sealing base for sealing said release port to a target tissue, wherein when said release port is sealed to a target tissue a first therapeutic agent in said reservoir is substantially prohibited from release by said device other than through said release port into the target tissue, and an attachment mechanism to facilitate sealing of said release port to a target tissue, said attachment mechanism comprising at least one member of the group consisting of a sufficient amount of an adhesive for adhering said sealing base to a target tissue wherein said adhesive is held within at least one cavity or channel within said sealing base, a suture holder for engaging at least one suture operatively attached to the surrounding tissue, and a band for engaging said device with a target tissue, wherein said reservoir comprises a first cavity that is connected to a first refilling port through a first tube.

2. The device of claim 1, wherein said first tube is connected to said housing via a protruding part that permits said first cavity to communicate with said reservoir.

3. The device of claim 2, wherein said first refilling port comprises a first refilling port cavity.

4. The device of claim 1, wherein said first refilling port can be implanted at a different site from the device location.

5. The device of claim 1, wherein said first refilling port comprises at least one septum.

6. The device of claim 5, wherein said at least one septum comprises a self-sealing material selected from the group consisting of latex, a synthetic rubber and a silicone elastomer.

7. The device of claim 5, wherein said septum is identifiable by imaging techniques selected from the group consisting of magnetic resonance imaging, x-ray, computerized tomography and ultrasound.

8. The device of claim 1, wherein said reservoir has at least a second cavity, said second cavity connected to a second refilling port through a second tube.

9. The device of claim 1, wherein said first refilling port is shaped to facilitate its implantation onto or into tissues.

10. The device of claim 1, wherein said first refilling port comprises a pump.

11. The device of claim 10, wherein said pump is a mechanical pump.

12. The device of claim 1, wherein said therapeutic agent is a prophylactic agent.

13. The device of claim 1, wherein said attachment mechanism comprises an adhesive layer.

14. The device of claim 13, wherein said adhesive layer can be applied during implantation of said device.

15. The device of claim 13, wherein said adhesive layer comprises a pressure-sensitive adhesive.

16. The device of claim 15, wherein said pressure-sensitive adhesive is selected from the group consisting of a hydrocolloid, a hydrogel, an acrylate and a silicone.

17. The device of claim 13, wherein said adhesive layer comprises a release liner.

18. The device of claim 1, wherein said reservoir carries a solid, liquid, viscous or gel-state therapeutic agent.

19. The device of claim 1, wherein said release port comprises a structural element to retain a therapeutic agent in said reservoir, wherein said structural element comprises one of the group consisting of a crossing band, a strip, a net and flanges.

20. The device of claim 19, wherein said structural element comprises at least one biocompatible and non-dissolvable material selected from the group consisting of a poly-ester, a poly-orthoester, a silicone, a polyethylene, a polypropylene, a polyurethane, and a metal.

21. The device of claim 19, wherein said structural element comprises at least one biocompatible and bioerodible material selected from the group consisting of glycolic acid, lactic acid, poly-ethylene-glycol, poly-vinyl-alcohol, poly-vinyl-pyrrolidone and methacrylates.

22. The device of claim 1, wherein said release port comprises a film that is permeable to a therapeutic agent to be placed in said reservoir.

23. The device of claim 22, wherein said film comprises at least one compound selected from the group consisting of a glycolic acid, a lactic acid, a poly-ethylene-glycol, a poly-vinyl-alcohol, a polyvinylpyrollidone, a methacrylates, cellulose, starch, ethylene vinyl acetate, and gelatin.

24. The device of claim 1, further comprising a pressure-controlled pump for providing therapeutic agent to said reservoir.

25. The device of claim 1, wherein said therapeutic agent is a diagnostic agent.

26. The device of claim 2, wherein said valve comprises a septum.

27. The structural element of claim 19, comprising a porous barrier.

28. The porous barrier of claim 27, wherein said porous barrier can control the diffusion interface between said reservoir and a targeted tissue.

29. The porous barrier of claim 27, comprising at least a first porous membrane.

30. The porous barrier of claim 27, comprising a membrane formed of a material selected from the group consisting of a poly-orthoester, a poly-glycolic acid, a poly-lactic acid, a poly-caprolactone, a polyvinyl-alcohol, a polyvinyl-pyrrilidone, hyaluronic acid, fibrin, methyl-cellulose, collagen, ethylene vinyl acetate, a polyethylene, a polyurethane, a metal, and gelatin.

31. An implantable delivery device for delivery of at least a first therapeutic agent into a target tissue, comprising: a housing, said housing comprising a reservoir with a drug release port for release of at least a first therapeutic agent into a target tissue, said reservoir having at least a first wall that is substantially impermeable to a first therapeutic agent to be placed therein, a sealing base for sealing said release port to a target tissue, wherein when said release port is sealed to a target tissue a first therapeutic agent in said reservoir is substantially prohibited from release by said device other than through said release port into the target tissue, and an attachment mechanism to facilitate sealing of said release port to a target tissue, said attachment mechanism comprising at least one member of the group consisting of a sufficient amount of an adhesive for adhering said sealing base to a target tissue, a suture holder for engaging at least one suture operatively attached to the surrounding tissue, and a band for engaging said device with a target tissue, further comprising an osmotic pump.

32. An implantable delivery device for delivery of at least a first therapeutic agent into a target tissue, comprising: a housing, said housing comprising a reservoir with a drug release port for release of at least a first therapeutic agent into a target tissue, said reservoir having at least a first wall that is substantially impermeable to a first therapeutic agent to be placed therein, a sealing base for sealing said release port to a target tissue, wherein when said release port is sealed to a target tissue a first therapeutic agent in said reservoir is substantially prohibited from release by said device other than through said release port into the target tissue, and an attachment mechanism to facilitate sealing of said release port to a target tissue, said attachment mechanism comprising at least one member of the group consisting of a sufficient amount of an adhesive for adhering said sealing base to a target tissue, a suture holder for engaging at least one suture operatively attached to the surrounding tissue, and a band for engaging said device with a target tissue, further comprising at least one mechanism for retaining a solid or viscous therapeutic material in said reservoir.

33. An implantable delivery device for delivery of at least a first therapeutic agent into a target tissue, comprising: a housing, said housing comprising a reservoir with a drug release port for release of at least a first therapeutic agent into a target tissue, said reservoir having at least a first wall that is substantially impermeable to a first therapeutic agent to be placed therein, a sealing base for sealing said release port to a target tissue, wherein when said release port is sealed to a target tissue a first therapeutic agent in said reservoir is substantially prohibited from release by said device other than through said release port into the target tissue, and an attachment mechanism to facilitate sealing of said release port to a target tissue, said attachment mechanism comprising at least one member of the group consisting of a sufficient amount of an adhesive for adhering said sealing base to a target tissue, a suture holder for engaging at least one suture operatively attached to the surrounding tissue, and a band for engaging said device with a target tissue, further comprising at least one reinforcement mechanism for preventing collapse of said reservoir.

34. The device of claim 33, wherein said at least one reinforcement mechanism comprises metal.

* * * * *